(12) United States Patent  
Tatsutani et al.

(10) Patent No.: US 9,222,952 B2
(45) Date of Patent: Dec. 29, 2015

(54) SAMPLE PROCESSING SYSTEM, TRANSPORT CONTROL SYSTEM AND TRANSPORT CONTROL METHOD

(75) Inventors: Hiroo Tatsutani, Kobe (JP); Hiroyuki Tanaka, Halstenbek (DE)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 13/071,152

(22) Filed: Mar. 24, 2011

(65) Prior Publication Data

US 2011/0243792 A1   Oct. 6, 2011

(30) Foreign Application Priority Data

Mar. 31, 2010 (JP) ................. 2010-080163

(51) Int. Cl.
*G01N 35/02* (2006.01)
*G01N 35/04* (2006.01)
*G01N 35/00* (2006.01)

(52) U.S. Cl.
CPC ............ *G01N 35/04* (2013.01); *G01N 35/0092* (2013.01); *G01N 35/021* (2013.01); *G01N 2035/00752* (2013.01); *G01N 2035/0462* (2013.01); *G01N 2035/0465* (2013.01); *G01N 2035/0467* (2013.01); *G01N 2035/0493* (2013.01)

(58) Field of Classification Search
None
See application file for complete search history.

(56) References Cited

U.S. PATENT DOCUMENTS

| 6,290,907 B1 * | 9/2001 | Takahashi et al. ............... 422/65 |
| 6,599,749 B1 * | 7/2003 | Kodama et al. .................. 436/47 |
| 2007/0207056 A1 * | 9/2007 | Veiner et al. .................... 422/63 |

FOREIGN PATENT DOCUMENTS

| EP | 0 902 290 A2 | 3/1999 |
| JP | 58-27168 | 2/1983 |
| JP | 9-281113 | 10/1997 |
| JP | 11-304808 A | 11/1999 |
| JP | 11-316236 A | 11/1999 |
| JP | 2003-066050 A | 3/2003 |

* cited by examiner

Primary Examiner — P. Kathryn Wright
(74) Attorney, Agent, or Firm — Brinks Gilson & Lione

(57) ABSTRACT

A sample processing system comprising: first, second and third sample processing units; first, second and third sample transport units; and a control section is disclosed. In order to transport a sample rack which is to be introduced to the first sample transport unit to a destination sample transport unit which is located downstream of a second sample transport unit, the control section initially controls the first and second transport unit to move a transport member. When the sample rack arrives at a predetermined position on the transport path of the first transport unit, the control section controls the third transport unit to move a transport member.

10 Claims, 23 Drawing Sheets

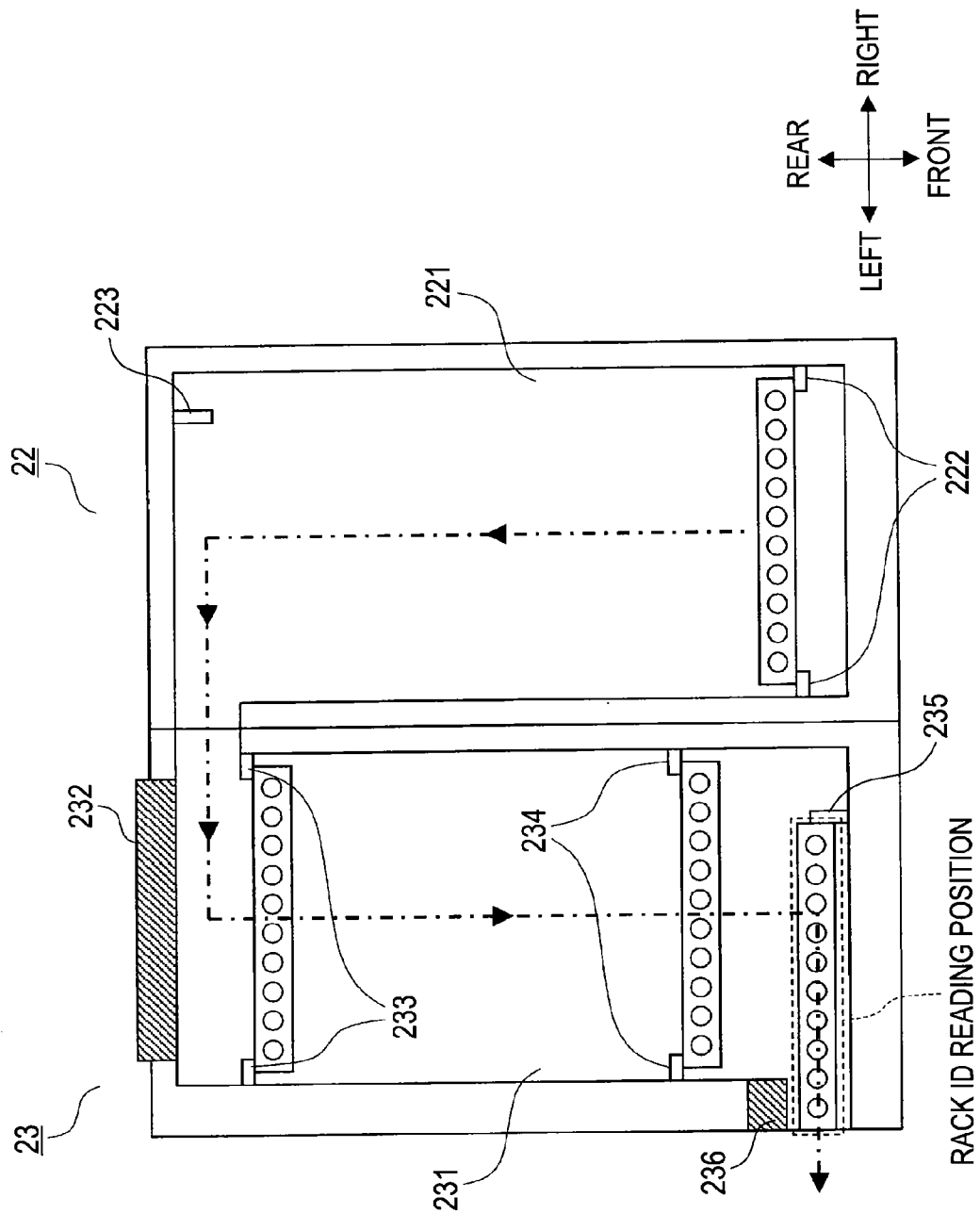

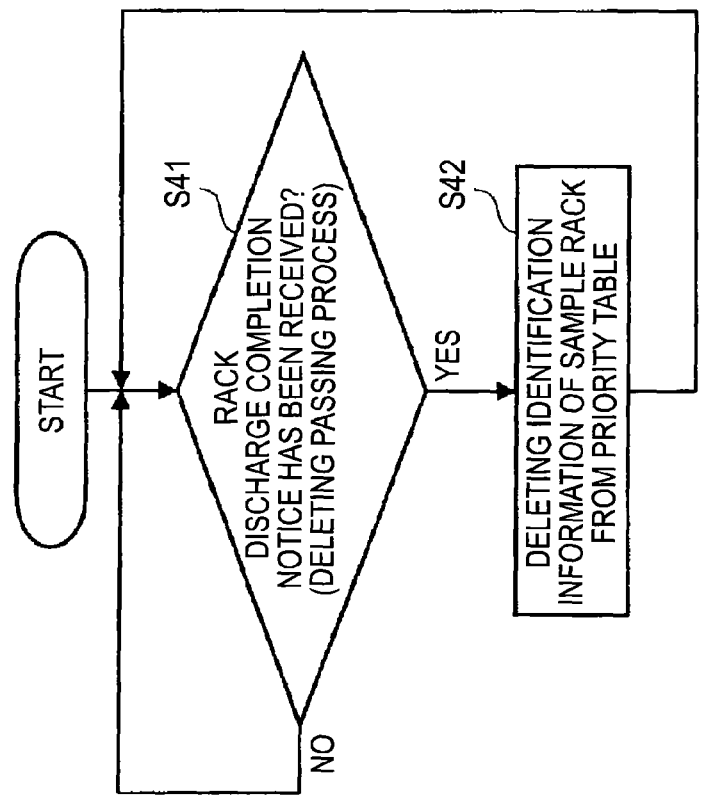
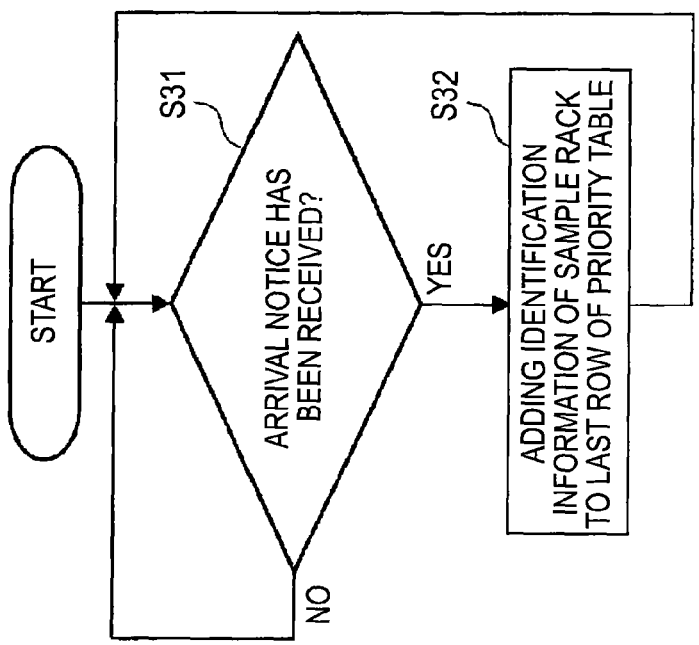

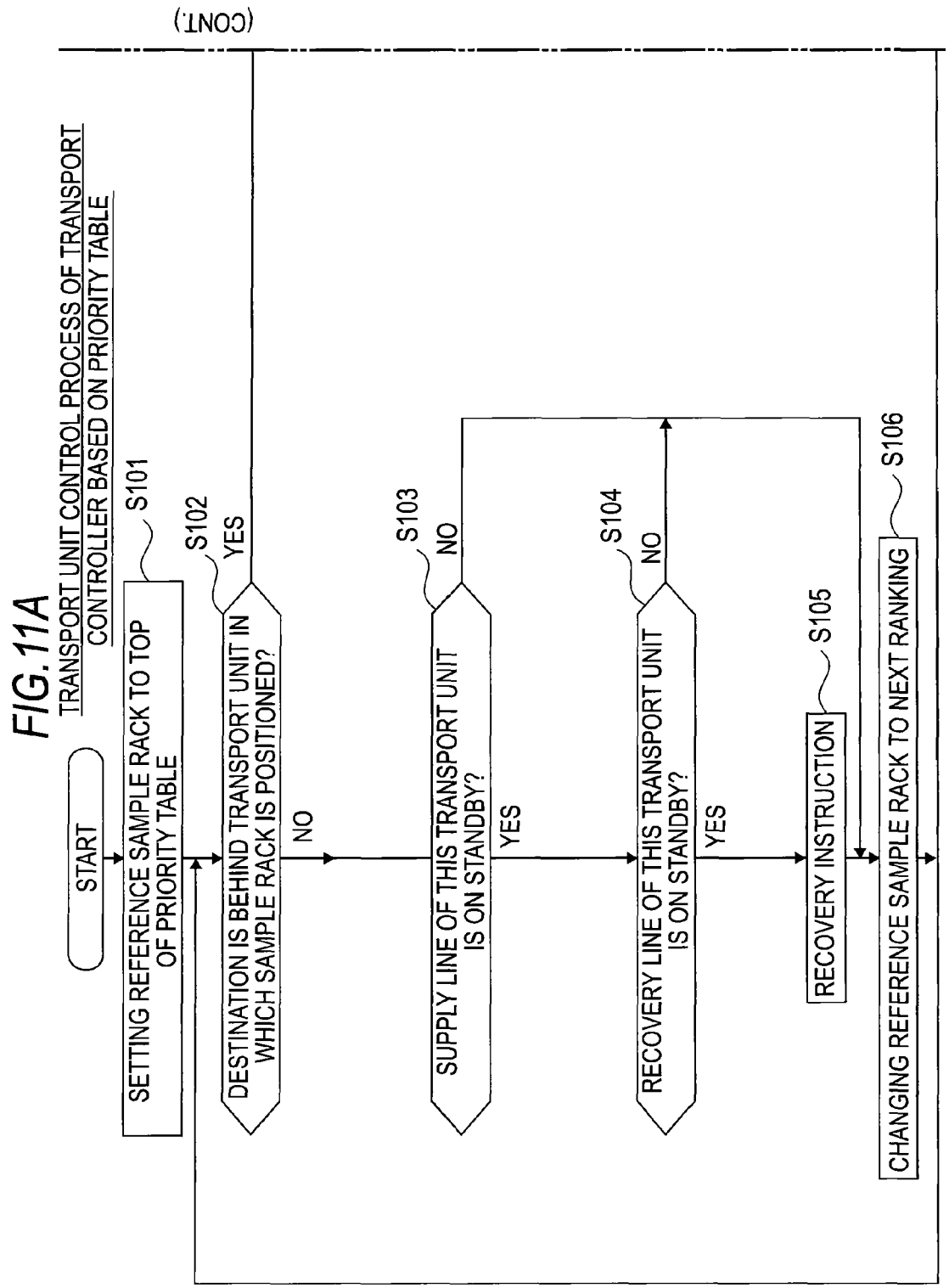

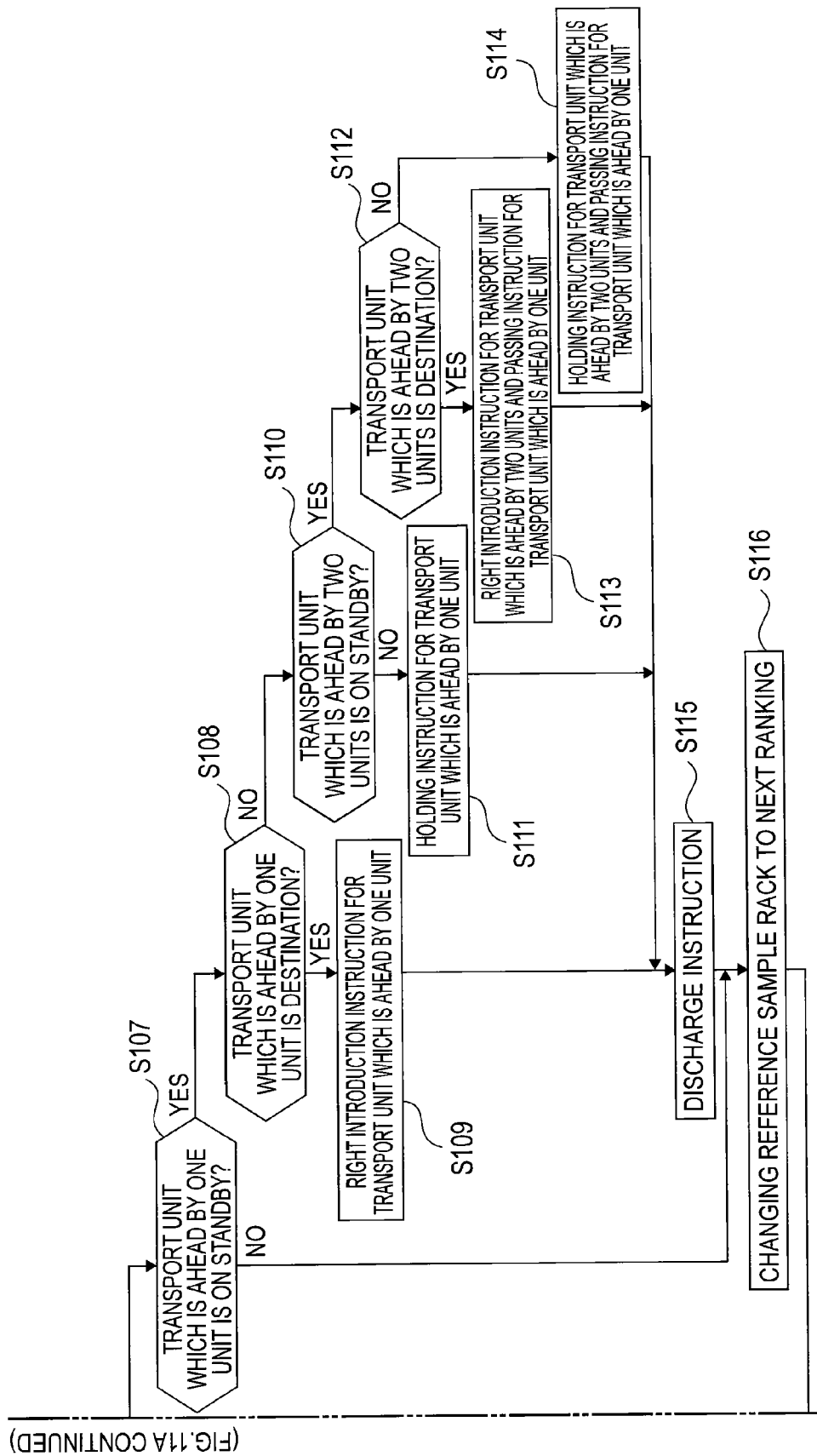

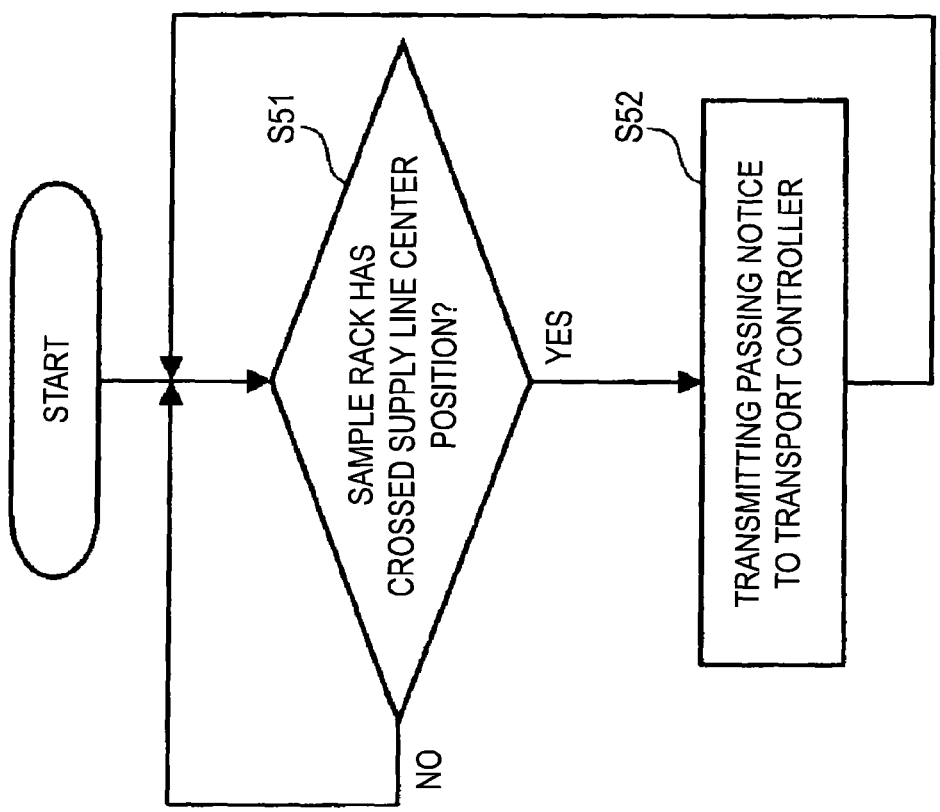
FIG.12 PASSING NOTIFICATION PROCESS OF TRANSPORT UNIT

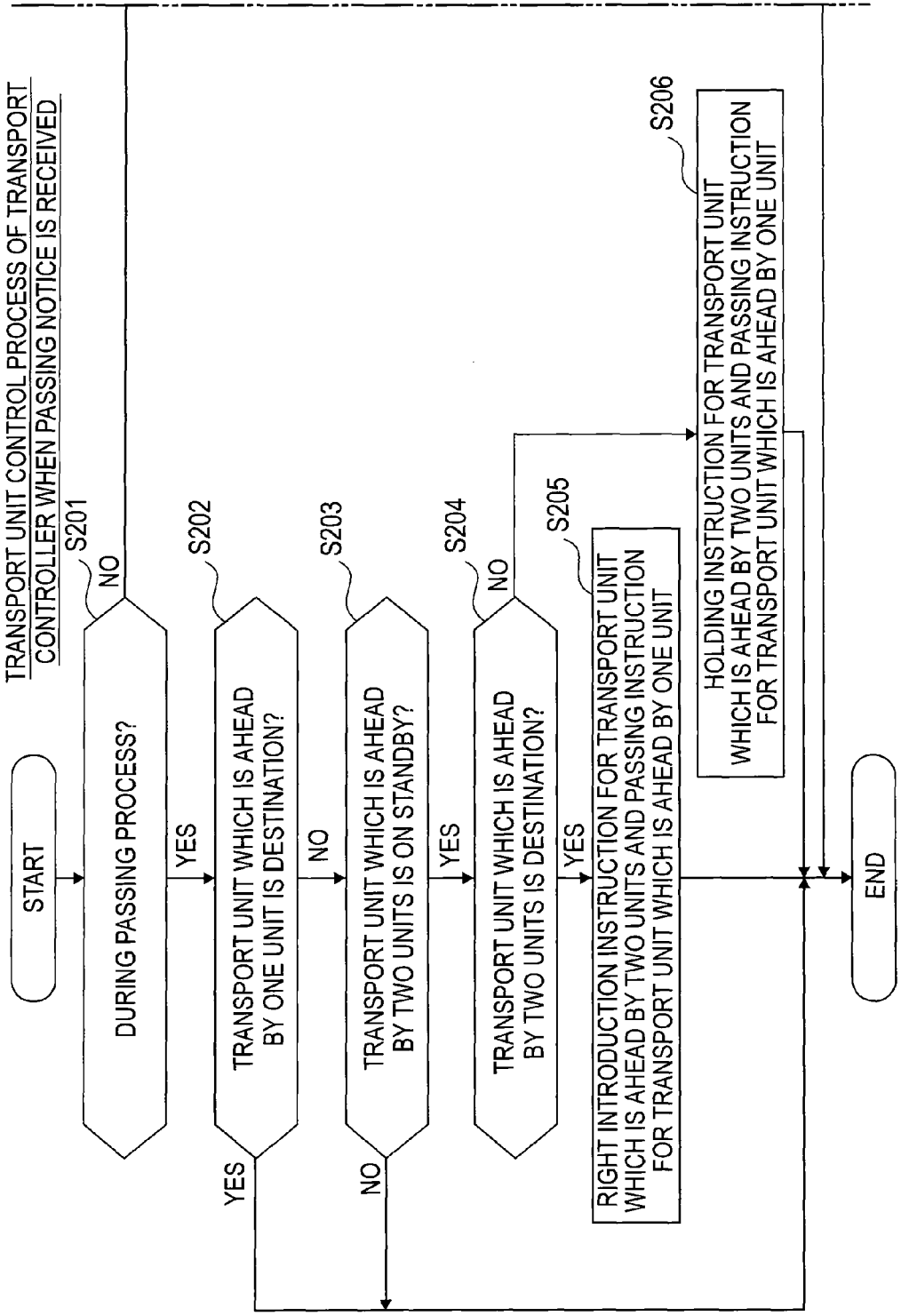

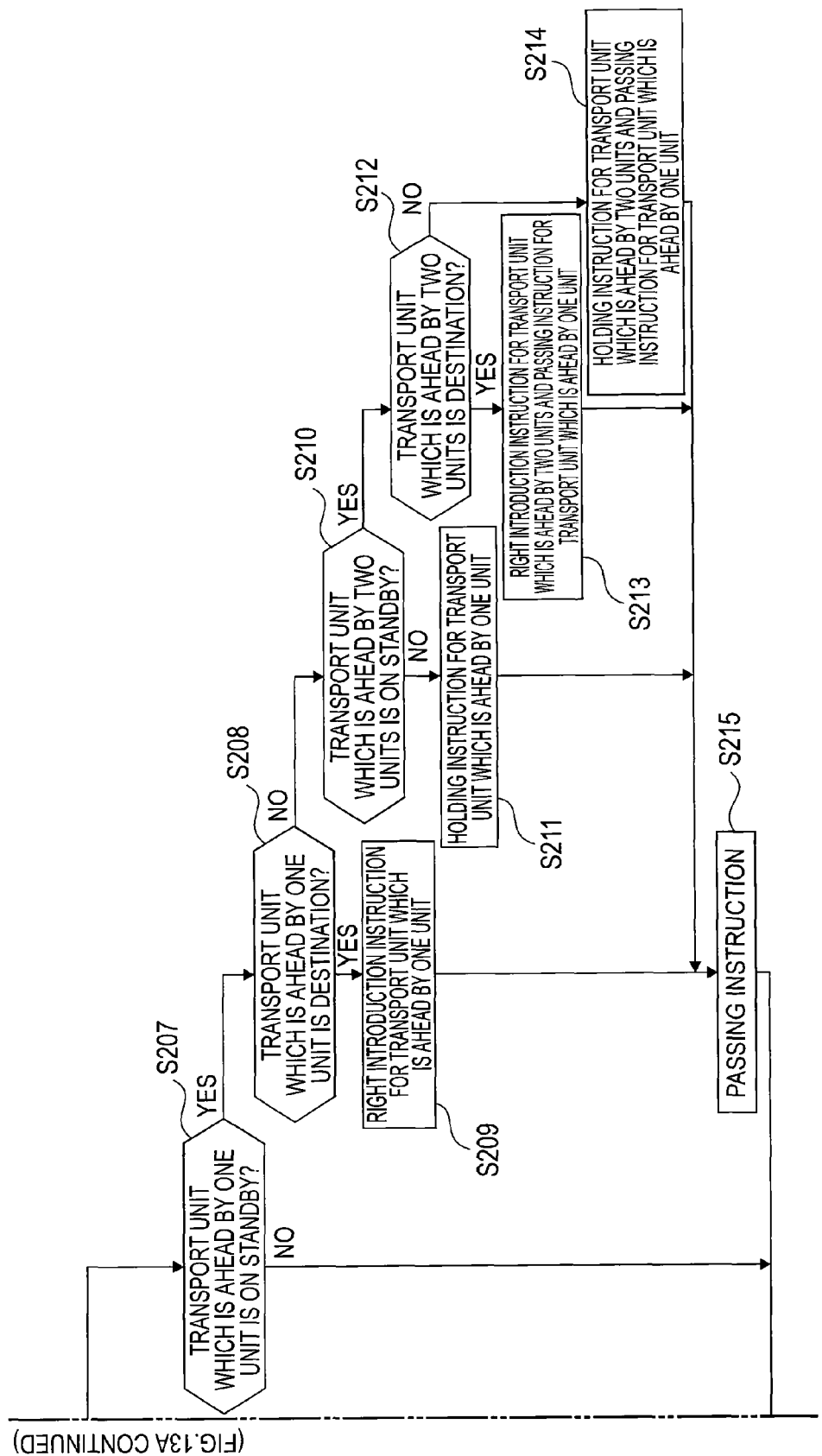

(B) HOLDING PROCESS OF TRANSPORT UNIT (A) PASSING PROCESS OF TRANSPORT UNIT

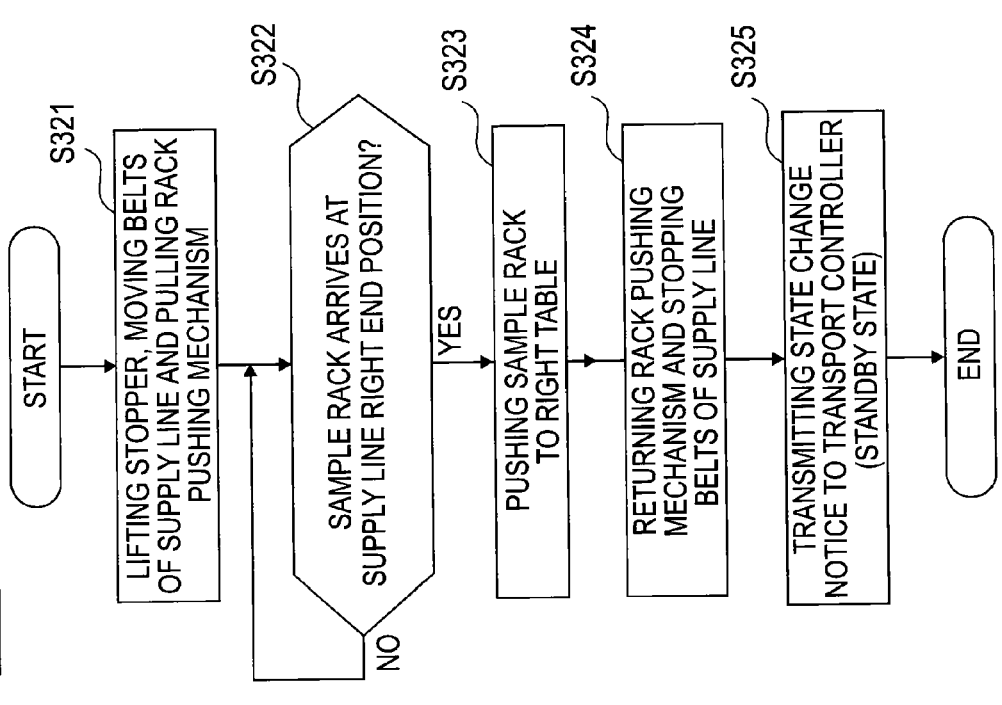

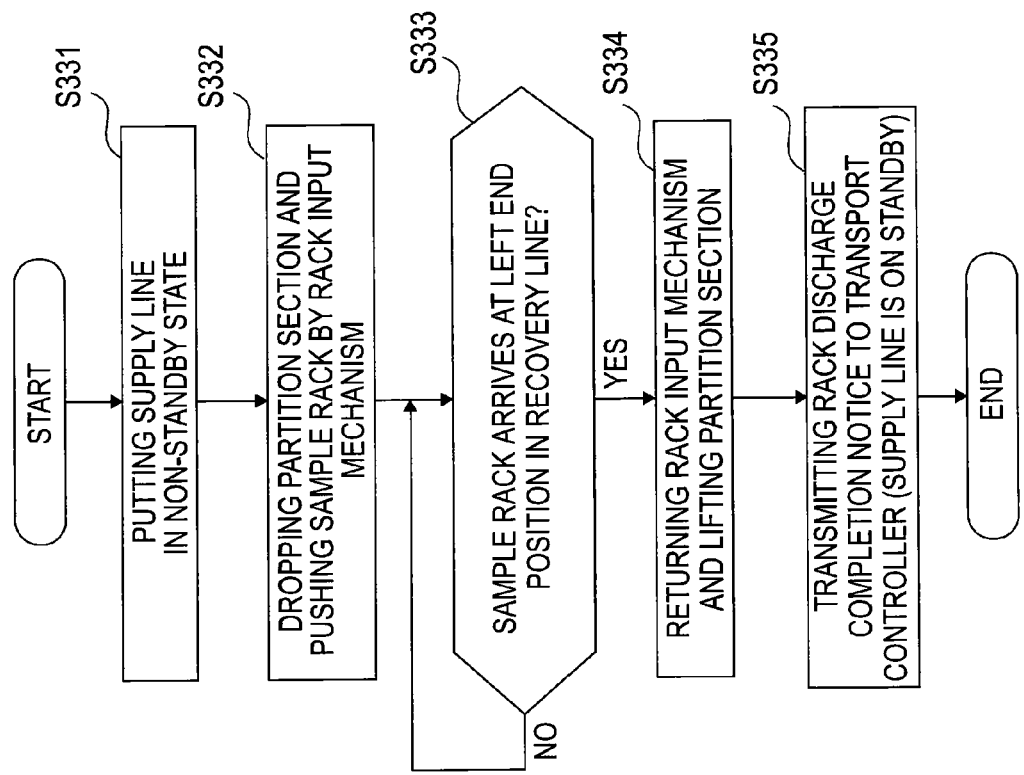
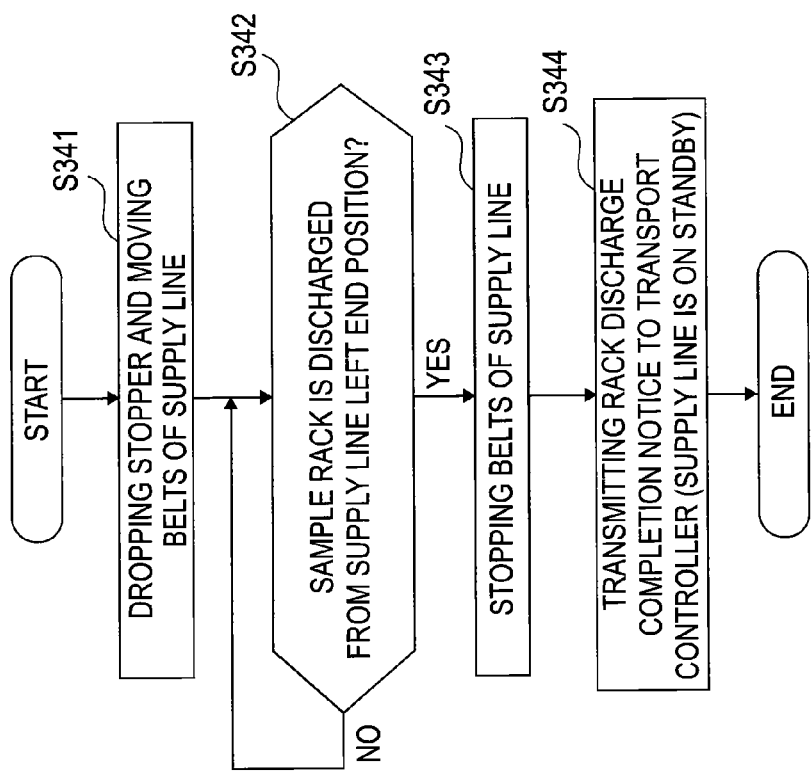

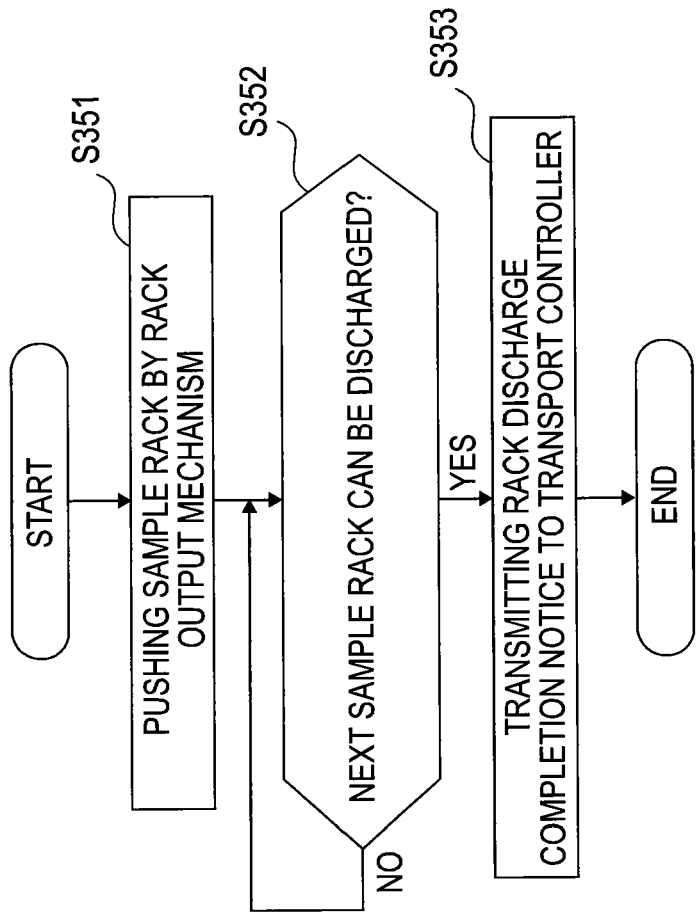

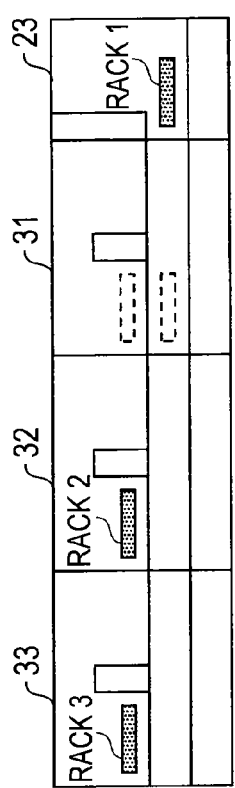
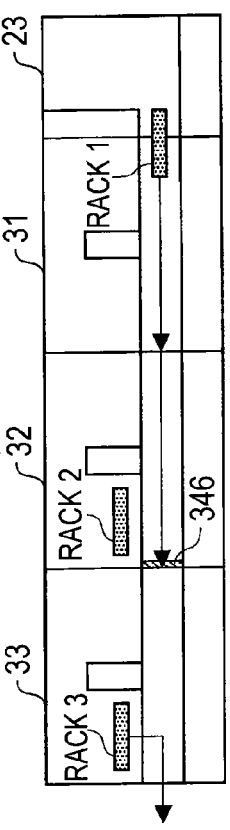
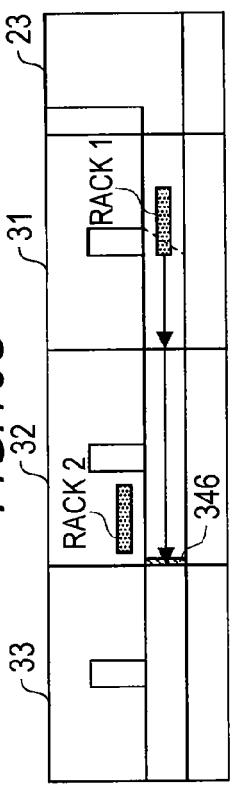
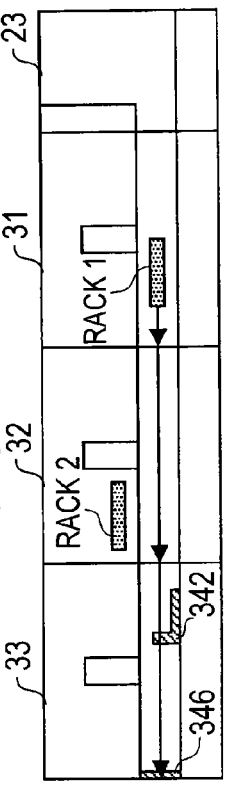

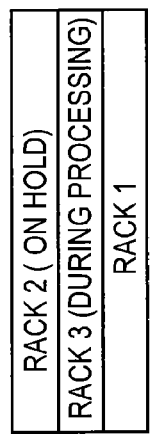
FIG.17E
FIG.17F
FIG.17G
FIG.17H
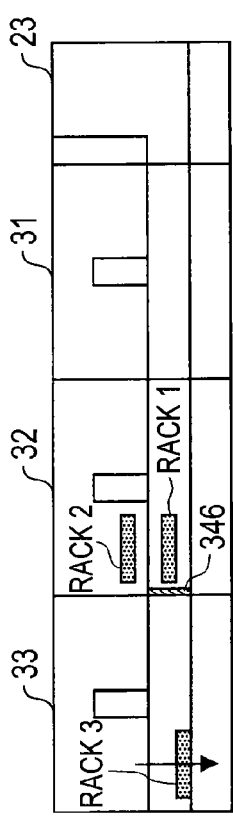
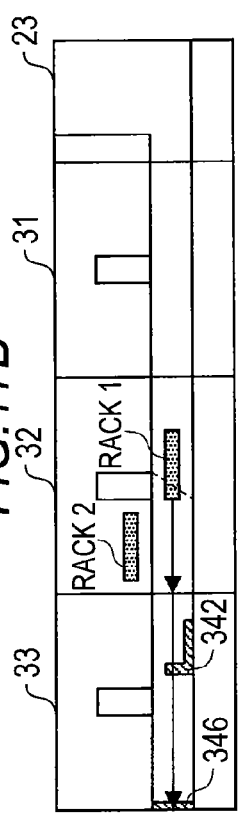
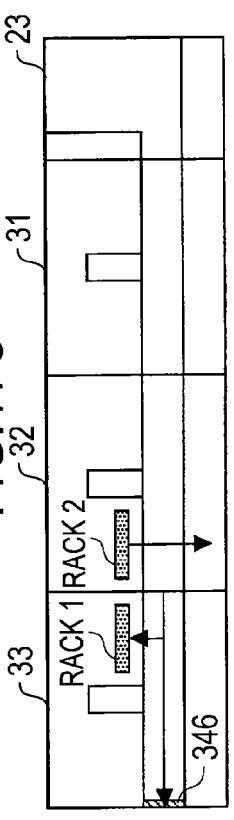
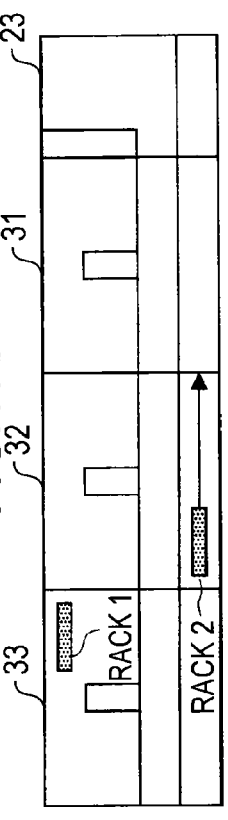
FIG.17A
FIG.17B
FIG.17C
FIG.17D

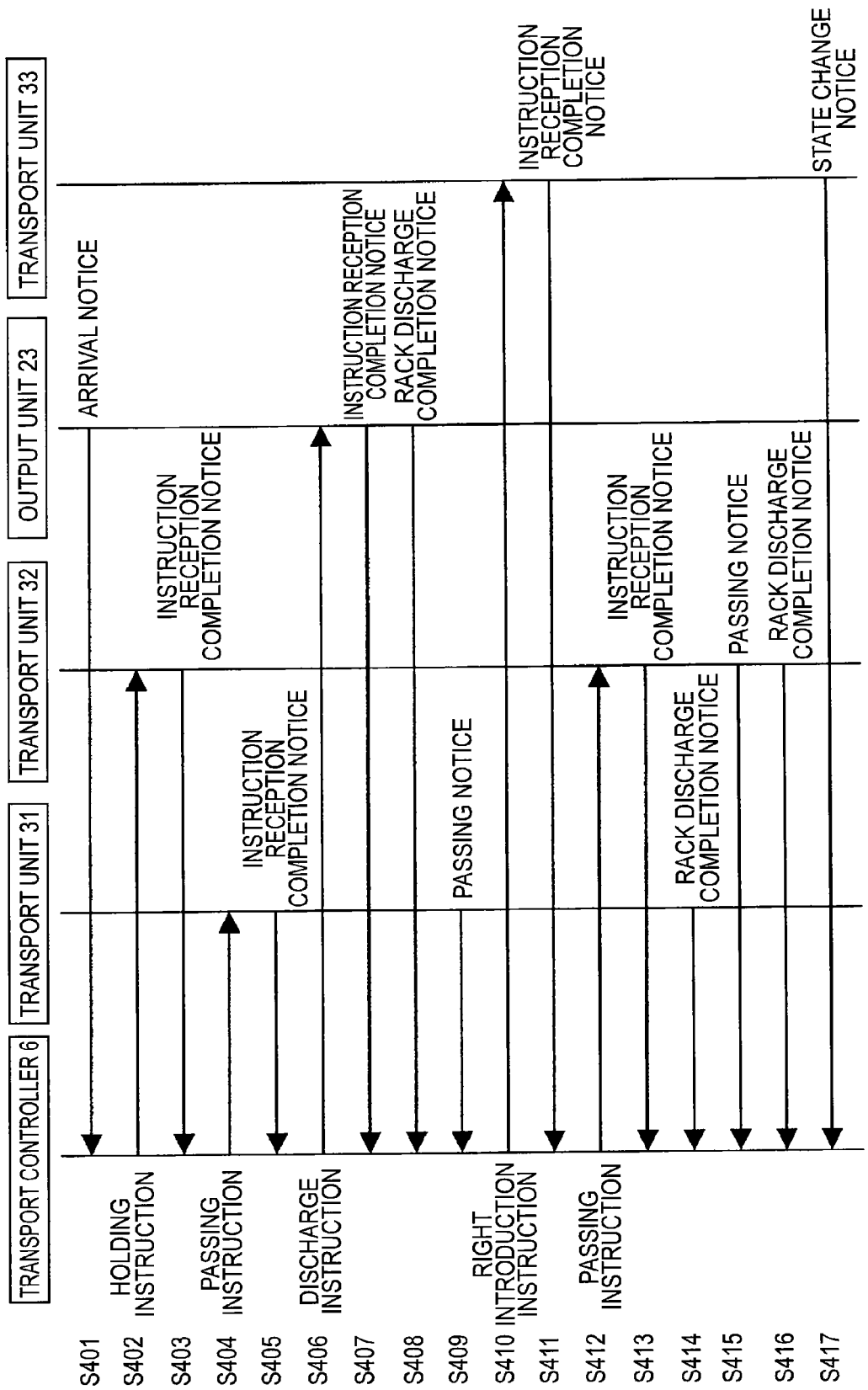

SAMPLE PROCESSING SYSTEM, TRANSPORT CONTROL SYSTEM AND TRANSPORT CONTROL METHOD

RELATED APPLICATIONS

This application claims priority under 35 U.S.C. §119 to Japanese Patent Application No. 2010-080163 filed on Mar. 31, 2010, the entire content of which is hereby incorporated by reference.

BACKGROUND OF THE INVENTION

1. Field of the Invention

The present invention relates to a sample processing system which includes a plurality of sample processing units and a transport unit transporting a sample to the plurality of sample processing units. The present invention also relates to a transport control system and a transport control method.

2. Description of the Related Art

In the past, sample processing systems have been known which include a plurality of sample processing units analyzing a sample such as blood or urine and a transport unit transporting a sample to the plurality of sample processing units.

For example, JP Laid-Open Patent Application No. 11-304808 discloses a sample processing system which includes three processing units, a transport line for transporting racks to these three processing units and a central control section. In this sample processing system, the transport line is divided into three transport line division units corresponding to the processing units, respectively. The central control section is configured to determine a transport destination of a sample rack from among the three processing units and control the operation of the transport line division unit so as to transport the sample rack to the determined transport destination.

In the above-described sample processing system, it is desirable to transport sample racks smoothly.

However, in the above-described Patent Document 1, it is not described in detail how to control the transport line division unit in order to transport a sample rack to the determined transport destination.

The present invention is contrived in view of the problem and an object thereof is to provide a sample processing system which can transport sample racks smoothly.

SUMMARY OF THE INVENTION

A first aspect of the present invention is a sample processing system comprising: a plurality of sample processing units; a plurality of sample transport units for transporting a sample rack to the plurality of sample processing units; and a control section, wherein the plurality of sample transport units includes at least a first sample transport unit, a second sample transport unit adjacent to the first sample transport unit and a third sample transport unit adjacent to the second sample transport unit in order from the upstream in a transport direction, each of the sample transport units includes a transport path for transporting a sample rack to another sample transport unit on the downstream side and a transport member for moving a sample rack on the transport path, and for transporting a sample rack which is to be introduced to the first sample transport unit to a destination sample transport unit which is located downstream of the second sample transport unit, the control section performs the following process including: moving the transport members of the first and second sample transport units; and when the sample rack arrives at a predetermined position in the transport path of the first sample transport unit, moving the transport member of the third sample transport unit.

A second aspect of the present invention is a sample processing system comprising: a plurality of sample processing units; m (m is an integer equal to or greater than 3) pieces of sample transport units for transporting a sample rack to each of the sample processing units, wherein each of the sample transport units has a transport path for transporting a sample rack to other sample transport units on the downstream side in a transport direction; and a control section, wherein in order to transport a target sample rack to an n-th (n is an integer equal to or greater than 3 and equal to or less than m) sample transport unit from a first sample transport unit to which the sample rack is next introduced, the control section controls the p (p is an integer equal to or greater than 2 and less than n) pieces of sample transport units from the first sample transport unit, and changes the control target to the p pieces of sample transport units from a second sample transport unit which are located next to the first sample transport unit when the target sample rack arrives at a predetermined position in the transport path of the first sample transport unit.

A third aspect of the present invention is a transport control system comprising at least one processor of a computer system and at least one memory that stores programs executable by the at least one processor to: store a table in which mobile objects are listable which are to be transported to their destination nodes selected among a plurality of nodes arranged along a transport path; add a mobile object to the table upon reception of a notice which notifies that said mobile arrives and is held at an en route node which is located en route to a destination node of said mobile object along the transport path; and remove the mobile object from the table upon reception of a notice which notifies that said mobile object moves out of the en route node.

A fourth aspect of the present invention is a transport control method comprising computer executable steps executed by at least one processor of a computer system to implement: controlling first and second sample transport units so as to move transport members to transport a sample rack which is to be introduced to the first sample transport unit toward a third sample transport unit; and controlling third sample transport unit so as to move a transport member when the sample rack arrives at predetermined position on the first transport unit.

BRIEF DESCRIPTION OF THE DRAWINGS

FIG. 3 is a plan view showing the configuration when an insertion unit and an output unit according to the embodiment are viewed from the upper side.

FIGS. 9A to 9D show flowcharts of an arrival notification process of the transport unit, an arrival notification process of the output unit, a priority table addition process of the transport controller and a priority table deletion process of the transport controller according to the embodiment.

FIGS. 11A and 11B illustrate a flowchart showing a transport unit control process of the transport controller based on the priority table according to the embodiment.

FIG. 12 is a flowchart showing a passing notification process of the transport unit according to the embodiment.

FIGS. 13A and 13B illustrate a flowchart showing a transport unit control process of the transport controller when receiving a passing notice according to the embodiment.

FIGS. 14A to 14C show flowcharts showing a passing process, a holding process and a right introduction process of the transport unit according to the embodiment.

FIGS. 15A to 15C show flowcharts showing a recovery process and a discharge process of the transport unit and a discharge process of the output unit according to the embodiment.

FIGS. 16A to 16H illustrate that the control of the transport units according to the embodiment.

FIGS. 17A to 17H illustrate that a sample rack is transported up to a destination by controlling the transport units according to the embodiment.

FIG. 18 is a diagram showing the contents of the communication which is performed between the transport units, the output unit and the transport controller according to the embodiment.

DETAILED DESCRIPTION OF THE PREFERRED EMBODIMENT

This embodiment is a sample processing system for examination and analysis related to blood, to which the present invention is applied. A sample processing system according to this embodiment includes three measuring units and one smear preparation apparatus. In the three measuring units, blood analysis is performed in parallel, and when it is necessary to prepare a smear based on the analysis result thereof, the smear preparation apparatus prepares a smear.

Hereinafter, a sample processing system according to this embodiment will be described with reference to the drawings.

Figure 1:
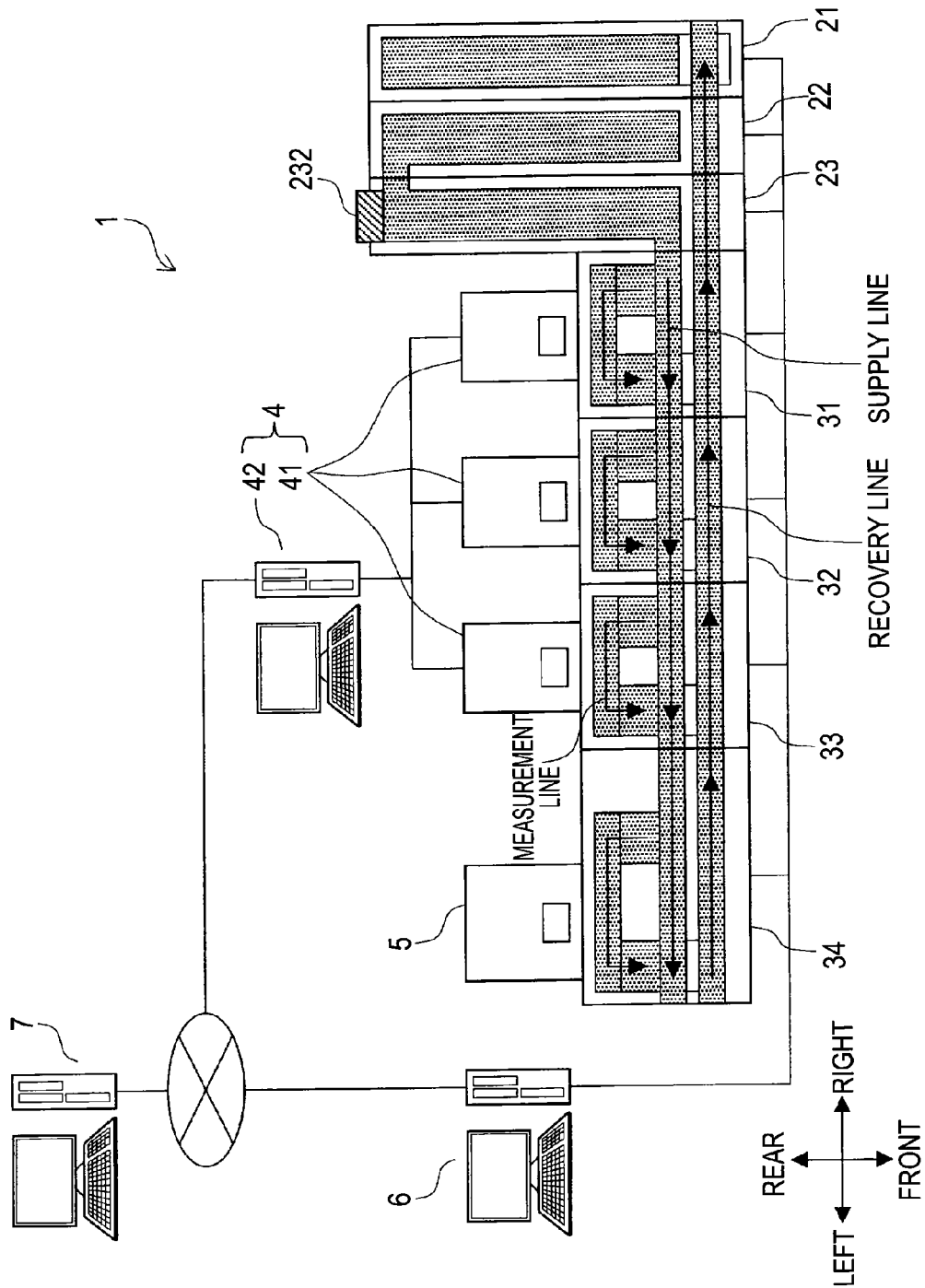
FIG. 1 is a plan view schematically showing the configuration when a sample processing system according to an embodiment is viewed from the upper side.

FIG. 1 is a plan view schematically showing the configuration when a sample processing system 1 is viewed from the upper side.

The sample processing system 1 according to this embodiment is configured to include a recovery unit 21, an insertion unit 22, an output unit 23, transport units 31 to 34, a blood cell analysis apparatus 4, a smear preparation apparatus 5 and a transport controller 6. In addition, the sample processing system 1 of this embodiment is connected to a host computer 7 via a communication network so as to communicate therewith.

Each of the recovery unit 21, the insertion unit 22 and the output unit 23 is configured so that a plurality of sample racks can be placed therein.

Figure 2A:
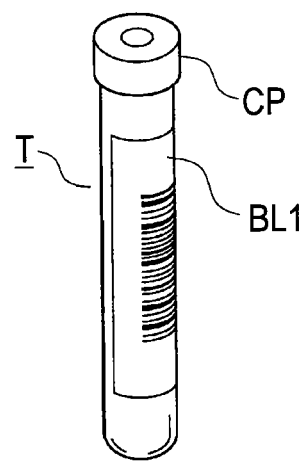
FIGS. 2A and 2B are diagrams showing the configurations of a sample container and a sample rack according to the embodiment.
Figure 2B:
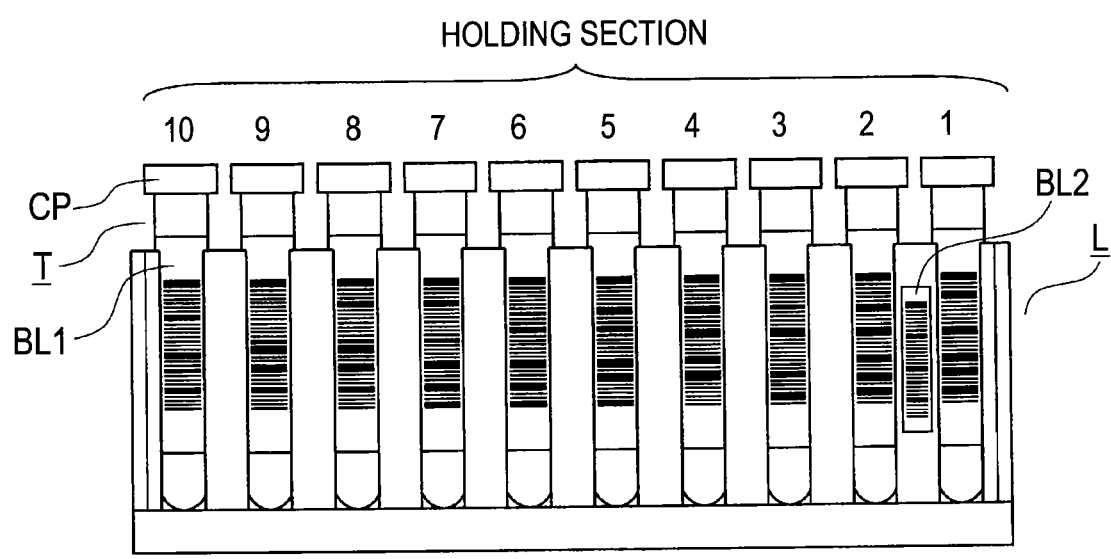

FIG. 2 is a diagram showing the configurations of a sample container T and a sample rack L. FIG. 2A is a perspective view showing the appearance of a sample container T and FIG. 2B is a front view of a sample rack L.

Referring to FIG. 2A, a sample container T is a tubular container made of glass or a synthetic resin having translucency and the upper end thereof is opened. In the sample container, a blood sample collected from a patient is contained and the opening of the upper end is sealed by a cap section CP. A bar-code label BL1 is adhered to a side surface of the sample container T. A bar-code showing a sample ID is printed on the bar-code label BL1.

Referring to FIG. 2B, in a sample rack L, ten holding sections are formed so as to arrange and hold ten sample containers T in a vertical state (erect state). In addition, as shown in the drawing, a bar-code label BL2 is adhered to a front surface of the sample rack L. A bar-code showing the rack ID is printed on the bar-code label BL2.

Returning to FIG. 1, the recovery unit 21 stores sample racks L in which analysis has ended. The insertion unit 22 stores sample racks L which are inserted by a user, and outputs the stored sample racks L to the output unit 23. Using a bar-code reading section 232, the output unit 23 reads the rack ID of a sample rack L which is output from the insertion unit 22 and the sample IDs of sample containers T which are associated with the holding sections of the sample rack L. In addition, the output unit 23 outputs the sample rack L in which the reading of the bar-codes has been completed to the transport unit 31.

The transport units 31 to 34 are connected to each other so as to deliver sample racks L. The right end of the transport unit 31 is connected to the output unit 23 so as to deliver sample racks L. As shown in the drawing, the transport units 31 to 33 are disposed in front of three measuring units 41, respectively, and as shown in the drawing, the transport unit 34 is disposed in front of the smear preparation apparatus 5.

As shown in the drawing, in the transport units 31 to 33, two transport lines for transporting sample racks L are set by dividing cases into a case in which sample measurement is performed and a case in which sample measurement is not performed in the measuring units 41 respectively corresponding to the transport units. That is, when the measurement is performed in the measuring unit 41, sample racks L are transported along a "measurement line" which is shown by the Π-shaped, rear arrow. When the measurement is not performed in the measuring unit 41 and the measurement or the preparation of a smear is performed on the downstream side (left side), sample racks L are transported along a "supply line" which is shown by the left-pointing, intermediate arrow so as to skip the measuring unit 41. In addition, as shown in the drawing, in the transport units 31 to 33, a right-pointing transport line is set for transporting sample racks L to the recovery unit 21. That is, a sample rack L in which there is no need to perform the measurement or the preparation of a smear on the downstream side (left side) is transported along a "recovery line" which is shown by the right-pointing, front arrow to be recovered by the recovery unit 21. As in the transport units 31 to 33, a measurement line, a supply line and a recovery line are also set in the transport unit 34 as shown in the drawing.

The blood cell analysis apparatus 4 is an optical flow cytometry type multiple blood cell analysis apparatus and includes the three measuring units 41 and an information processing apparatus 42.

The three measuring units 41 take a sample container T from a sample rack L at a predetermined position on the measurement line of the transport units 31 to 33, which are disposed in front of the measuring units, respectively, and measure a sample in the sample container T. That is, the measuring unit 41 measures the sample contained in the sample container T by moving the sample container T taken from the sample rack L into the measuring unit 41. When the measurement in the measuring unit 41 is completed, the measuring unit 41 returns this sample container T to the original holding section in the sample rack L.

The information processing unit 42 is connected to the three measuring units 41 so as to communicate therewith, and controls the operations of the three measuring units 41. In addition, the information processing unit 42 is also connected to the host computer 7 via a communication network so as to communicate therewith and inquires of the host computer 7 for measurement orders which are performed by the measuring unit 41. That is, when a sample ID of the sample container T which is moved into the measuring unit 41 is read by a bar-code reader (not shown) in the measuring unit 41, the information processing unit 42 inquires of the host computer 7 for measurement orders of this sample. After that, the information processing unit 42 controls the measurement operation of the measuring unit 41 on the basis of the measurement order received from the host computer 7. In addition, the information processing unit 42 performs analysis on the basis of the result of the measurement performed by the measuring unit 41.

The smear preparation apparatus 5 suctions a sample which is contained in a sample container T at a predetermined position on the measurement line of the transport unit 34 disposed forward and prepares a smear of this sample. Whether or not to prepare a smear is determined by the transport controller 6 on the basis of the result of the analysis performed by the information processing unit 42. When the transport controller 6 determines that the preparation of a smear is needed, a sample rack L containing a sample which is a target is transported along the measurement line of the transport unit 34 and a smear is prepared in the smear preparation apparatus 5.

The transport controller 6 is connected to the recovery unit 21, the insertion unit 22, the output unit 23 and the transport units 31 to 34 so as to communicate therewith and controls the operations of the units. In addition, the transport controller 6 is connected to the host computer 7 via a communication network so as to communicate therewith. The transport controller 6 inquires of the host computer 7 for measurement orders when receiving from the output unit 23 the rack ID of the sample rack L and the sample ID of the sample container T which is associated with the holding section in the sample rack L. In addition, the transport controller 6 determines a transport destination of the sample rack L and controls the transport units 31 to 34 so as to efficiently transport the sample rack L. Such control of the transport units 31 to 34 will be described later with reference to FIGS. 9 to 18.

FIG. 3 is a plan view showing the configuration when the insertion unit 22 and the output unit 23 are viewed from the upper side. In FIG. 3, a portion which transports a sample rack L in the right direction along the recovery line is omitted for the sake of convenience.

When a sample rack L is inserted onto a transport passage 221 of the insertion unit 22, a rack input mechanism 222 moves backward while engaging with the front ends of the sample rack L and this sample rack L is sent to the rear position in the transport passage 221. The right side surface of the sample rack L positioned at the rear position in the transport passage 221 is pressed by a rack output mechanism 223 and is thus output to the rear position in a transport passage 231 of the output unit 23. At the rear position in the transport passage 231, the bar-code reading section 232 reads the rack ID of the sample rack L and a sample ID of a sample container T in association with the holding section in the sample rack L.

Next, by a rack input mechanism 233, the sample rack L positioned at the rear position in the transport passage 231 is sent to a position moving forward by a width in the front-back direction of the sample rack L from the rear position in the transport passage 231. Next, a rack input mechanism 234 moves forward while engaging with the rear ends of the sample rack L and the sample rack L is sent to the front position in the transport passage 231. The right side surface of the sample rack L positioned at the front position in the transport passage 231 is pressed by a rack output mechanism 235 and thus the sample rack L is moved in the left direction.

In this case, when the sample rack L is slightly moved to the left from the front position in the transport passage 231 and thus a bar-code label BL2 of the sample rack L is positioned in front of a bar-code reading section 236, the rack ID is read by the bar-code reading section 236. Hereinafter, the position of the sample rack L at this time is called a "rack ID reading position". The transport controller 6 determines the measuring unit 41 or the smear preparation apparatus 5 which is a transport destination of this sample rack L on the basis of the rack ID read. After that, the sample rack L at the rack ID reading position is further pushed in the left direction by the rack output mechanism 235 and output to the transport unit 31.

Figure 4:
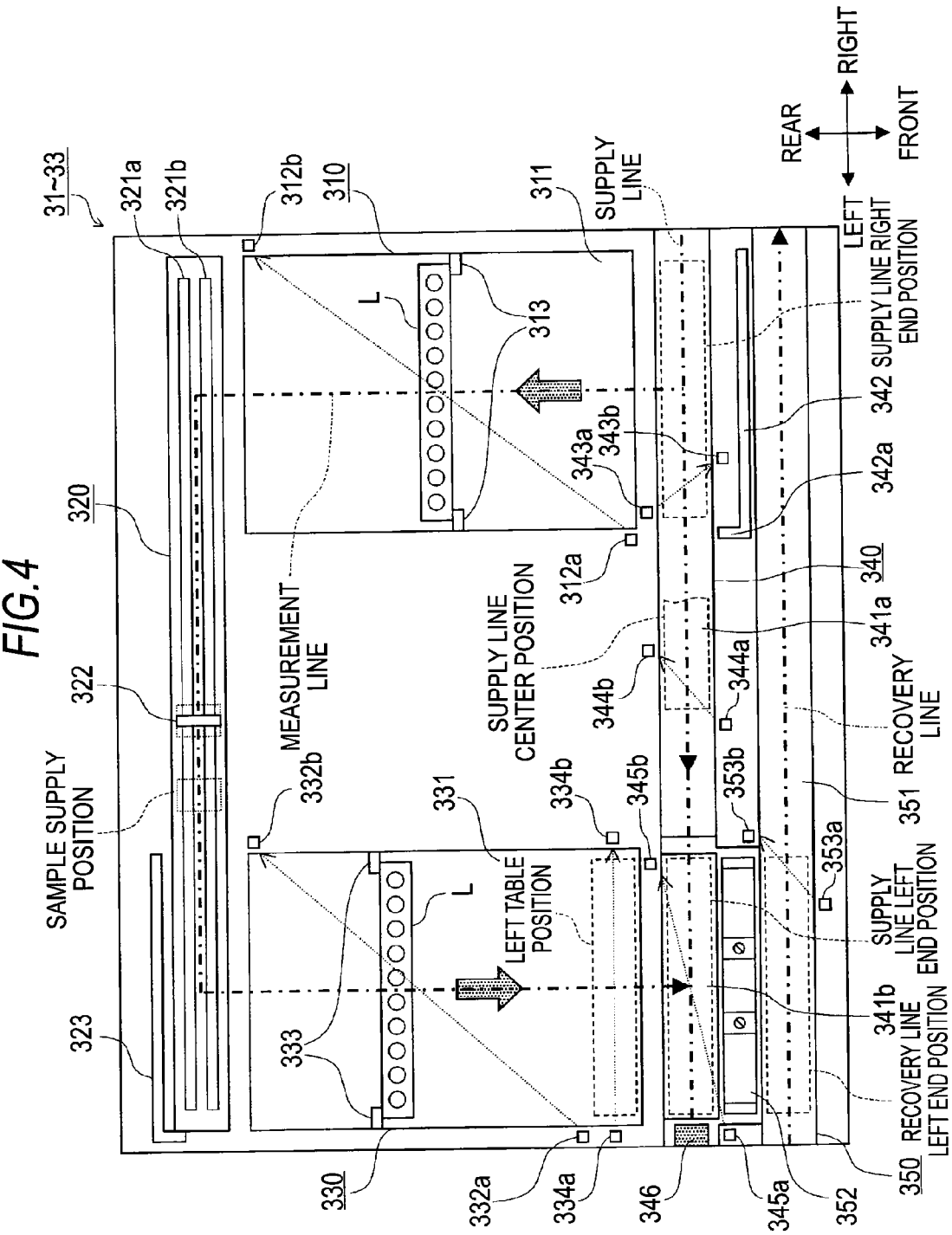
FIG. 4 is a plan view showing the configuration when a transport unit according to the embodiment is viewed from the upper side.

FIG. 4 is a plan view showing the configuration when the transport units 31 to 33 are viewed from the upper side. The transport units 31 to 33 includes a right table 310, a rack transport section 320, a left table 330 and rack transport sections 340 and 350. The measurement line of FIG. 1 is configured by the right table 310, the rack transport section 320 and the left table 330. In addition, the supply line of FIG. 1 is configured by the rack transport section 340 and the recovery line of FIG. 1 is configured by the rack transport section 350. The transport units 31 to 33 have the same configuration.

When the measurement of a sample rack L which is output from the upstream side (right side) is not performed in the measuring unit 41 corresponding to this transport unit, this sample rack L is linearly sent to the left end from the right end of the rack transport section 340 along the supply line by belts 341a and 341b of the rack transport section 340.

Here, transmission type sensors 344a and 344b are installed in the vicinity of the center of the rack transport section 340. The sensors 344a and 344b detect a sample rack L passing through a center position (hereinafter, referred to as a "supply line center position") in the rack transport section 340. In addition, transmission type sensors 345a and 345b are installed in the vicinity of the left end of the rack transport section 340. The sensors 345a and 345b detect a sample rack L passing through a left end position (hereinafter, referred to as a "supply line left end position") in the rack transport section 340 or a sample rack L positioned at the supply line left end position.

In addition, a stopper 346 is installed at the left end of the rack transport section 340. When the stopper 346 is lifted, that is, when the upper surface of the stopper 346 is positioned higher than the upper surface of the belt 341b, a sample rack L sent to the left end from the right end along the supply line is brought into contact with the side surface of the stopper 346 and stopped at the supply line left end position. On the other hand, when the stopper 346 is dropped, that is, when the upper surface of the stopper 346 is positioned as high as the upper surface of the belt 341b, a sample rack L sent to the left end from the right end along the supply line is output to the transport unit on the downstream side (left side) without being brought into contact with the stopper 346.

Next, when the measurement of a sample rack L which is output from the upstream side (right side) is performed in the measuring unit 41 corresponding to this transport unit, this sample rack L is positioned at the right end position (hereinafter, referred to as a "supply line right end position") in the rack transport section 340. That is, a rack pushing mechanism 342 is moved backward so that a wall section 342a slightly protrudes to the supply line from the state shown in the drawing. Accordingly, the sample rack L output from the upstream side is brought into contact with the wall section 342a and is thus stopped. In addition, transmission type sensors 343a and 343b are installed in the vicinity of the supply line right end position. The sensors 343a and 343b detect a sample rack L which is positioned at the supply line right end position.

Next, by further moving the rack pushing mechanism 342 backward, the sample rack L is pushed to the front end of a transport passage 311 of the right table 310. When transmission type sensors 312a and 312b detect the sample rack L on the transport passage 311, a rack input mechanism 313 moves backward while engaging with the front ends of the sample rack L and the sample rack L is sent backward. When the sample rack L is sent up to the right end position in the rack transport section 320, belts 321a and 321b are driven and the sample rack L is sent in the left direction.

After that, the sample rack L arrives at the position of a sample container sensor 322. The sample container sensor 322 is a contact type sensor. When a detection target sample container T, which is held in the sample rack L, passes through the position right under the sample container sensor 322, the contact piece of the sample container sensor 322 is bent by the sample container T and thus the presence of the sample container T is detected.

At a sample supply position positioned on the left side of the position, at which the sample container T has been detected by the sample container sensor 322, by a distance corresponding to two sample containers, a hand section (not shown) of the measuring unit 41 grips the sample container T and takes the sample container T from the sample rack L. The removed sample container T returns to the sample rack L after used in the measurement in the measuring unit 41. While the sample container T returns to the sample rack L, the transportation of the sample rack L is temporally stopped.

In this manner, when the measurement of the samples in all of the sample containers T held in the sample rack L is completed, the sample rack L is sent up to the left end position in the rack transport section 320 by the belts 321a and 321b. After that, the sample rack L is sent to the rear end of a transport passage 331 of the left table 330 by a rack pushing mechanism 323. When transmission type sensors 332a and 332b detect the sample rack L on the transport passage 331, a rack input mechanism 333 moves forward while engaging with the rear ends of the sample rack L. In this manner, the sample rack L is sent to the front.

Transmission type sensors 334a and 334b are installed in the vicinity of the front of the left table 330. The sensors 334a and 334b detect a sample rack L which is positioned at a front position (hereinafter, referred to as a "left table position") in the left table 330.

Next, a partition section 352 which is in front of the left table 330 and is between the rack transport sections 340 and 350 is controlled to be opened and closed and the sample rack L is positioned in either of the rack transport sections 340 or 350.

As a result of the measurement by the measuring unit 41, when it is determined that the smear preparation apparatus 5 on the downstream side needs to perform the smear preparation or the measuring unit 41 on the downstream side needs to perform the measurement on sample containers T which are held in the sample rack L, the sample rack L is moved up to the supply line left end position in the rack transport section 340 by the rack input mechanism 333 in a state in which the rack transport sections 340 and 350 are partitioned by the partition section 352. The sample rack L which is positioned at the supply line left end position is detected by the sensors 345a and 345b which are installed in the vicinity of the supply line left end position. After that, this sample rack L is output to the sample transport unit on the downstream side by the belt 341b of the rack transport section 340 in a state in which the stopper 346 is dropped.

On the other hand, as a result of the measurement by the measuring unit 41, when it is determined that the smear preparation apparatus 5 on the down-stream side does not need to perform the smear preparation or the measuring unit 41 on the downstream side does not need to perform the measurement on sample containers T which are held in the sample rack L, the upper surface of the partition section 352 is dropped to be disposed at the same height as the upper surface of the belt 341b of the rack transport section 340 and the sample rack L is moved up to the left end position (hereinafter, referred to as a "recovery line left end position") in the rack transport section 350 by the rack input mechanism 333. In this manner, by the rack input mechanism 333, the sample rack L is moved across the rack transport section 340 from the left table 330 up to the recovery line left end position. The sample rack L which is positioned at the recovery line left end position is detected by sensors 353a and 353b which are installed in the vicinity of the recovery line left end position. After that, this sample rack L is moved in the right direction along the recovery line by the belt 351 of the rack transport section 350. The sample rack L which is transported along the recovery line is stored in the recovery unit 21.

The transport unit 34 has almost the same configuration as those of the transport units 31 to 33. In this case, when a sample rack L including a sample in which it is determined that it is necessary to prepare a smear is transported to the transport unit 34, the sample rack L is transported along the measurement line and a sample is suctioned from a sample container T which is positioned at the sample supply position. In addition, the smear preparation apparatus 5 prepares a smear. After that, the sample rack L is transported in the right direction toward the recovery unit 21 along the recovery line.

Figure 5:
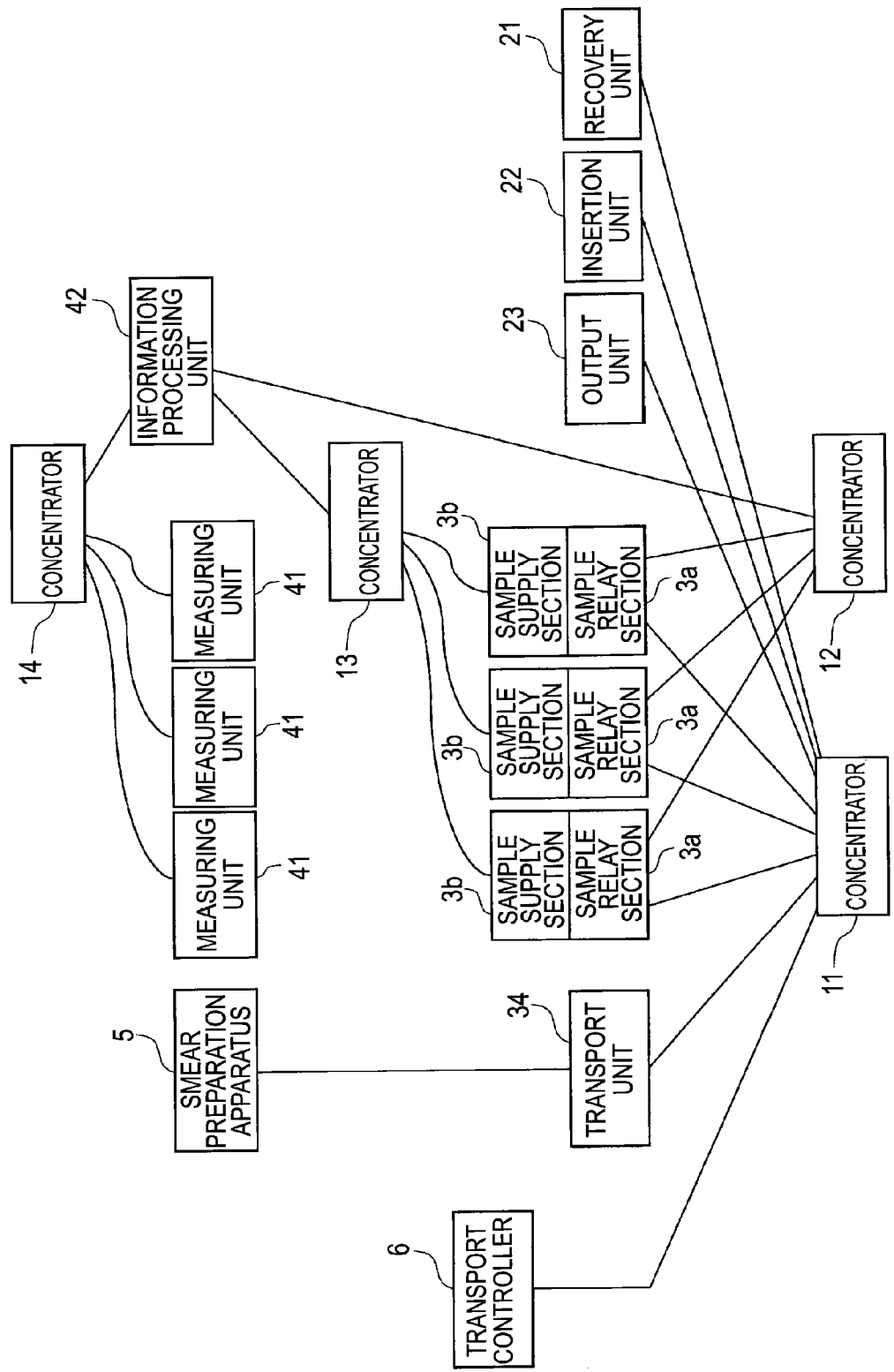
FIG. 5 is a diagram schematically showing the mutual connection relationships between the units (devices) in the sample processing system according to the embodiment.

FIG. 5 is a diagram schematically showing the mutual connection relationships between the units (devices) in the sample processing system 1.

Here, in the drawing, the transport units 31 to 33 are divided into a sample relay section 3a and a sample supply section 3b, respectively. In greater detail, the sample relay section 3a includes the left table 330 and the rack transport sections 340 and 350 of FIG. 4, and one of the neighboring two transport units receives a sample rack L and transports it to the other sample transport unit 3. The sample supply section 3b includes the right table 310 and the rack transport section 320 of FIG. 4 and transports a sample rack L to the sample supply position in order to measure a sample by the measuring unit 41.

The recovery unit 21, the insertion unit 22, the output unit 23, the three sample relay sections 3a, the transport unit 34 and the transport controller 6 are connected to a concentrator 11 so as to communicate therewith. The three sample relay sections 3a and the information processing unit 42 are connected to a concentrator 12 so as to communicate therewith. The three sample supply sections 3b and the information processing unit 42 are connected to a concentrator 13 so as to communicate therewith. The three measuring units 41 and the information processing unit 42 are connected to a concentrator 14 so as to communicate therewith.

Figure 6:
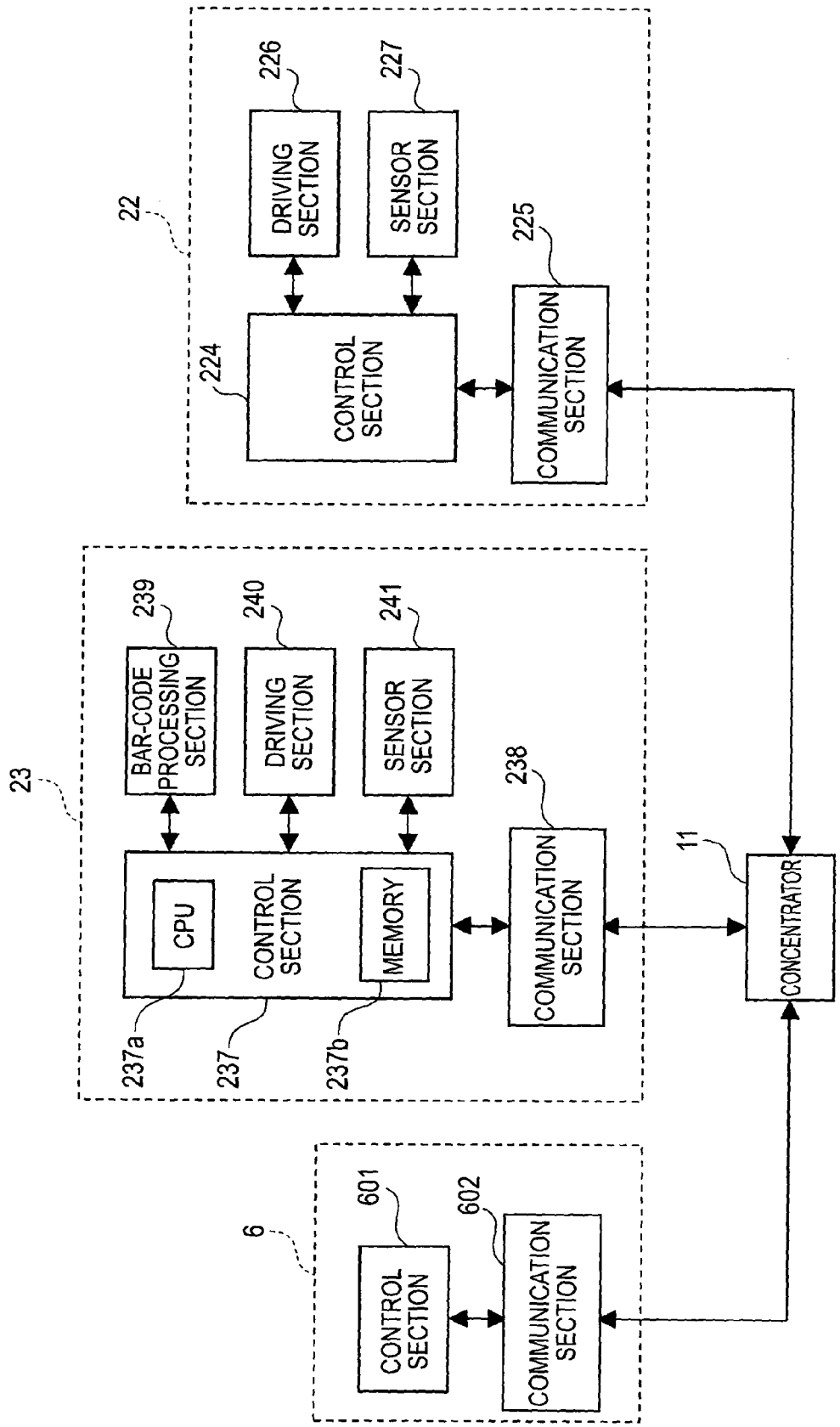
FIG. 6 is a diagram showing the outline of the configurations of the insertion unit, the output unit and the transport controller according to the embodiment.

FIG. 6 is a diagram showing the outline of the configurations of the insertion unit 22, the output unit 23 and the transport controller 6.

The output unit 23 includes a control section 237, a communication section 238, a bar-code processing section 239, a driving section 240 and a sensor section 241.

The control section 237 includes a CPU 237a and a memory 237b and executes a computer program which is stored in the memory 237b by the CPU 237a, and thus the sections are controlled in accordance with the control section of the transport controller 6. Another control section to be described later also includes a CPU and a memory. The communication section 238 includes a communication interface for performing data communication with an external device on the basis of Ethernet (registered trademark) standards and performs data communication with the concentrator 11.

The bar-code processing section 239 includes bar-code reading sections 232 and 236 shown in FIG. 3. The bar-code processing section 239 is controlled by the control section 237 and bar-code information which is read by the bar-code processing section 239 is output to the control section 237.

The driving section 240 is controlled by the control section 237. In the driving section 240, a mechanism for transporting a sample rack L which is stored in the output unit 23 and a stepping motor for driving this mechanism are included. The sensor section 241 outputs a detection signal to the control section 237. In the sensor section 241, a sensor for detecting a sample rack L which is stored in the output unit 23 is included.

As shown in the drawing, the insertion unit 22 has a configuration in which the bar-code processing section 239 is removed from the output unit 23. As shown in the drawing, the transport controller 6 has a configuration in which the driving section 226 and the sensor section 227 are removed from the insertion unit 22, and includes a control section 601 and a communication section 602. The recovery unit 21 (not shown) also has the same configuration as that of the insertion unit 22.

Figure 7:
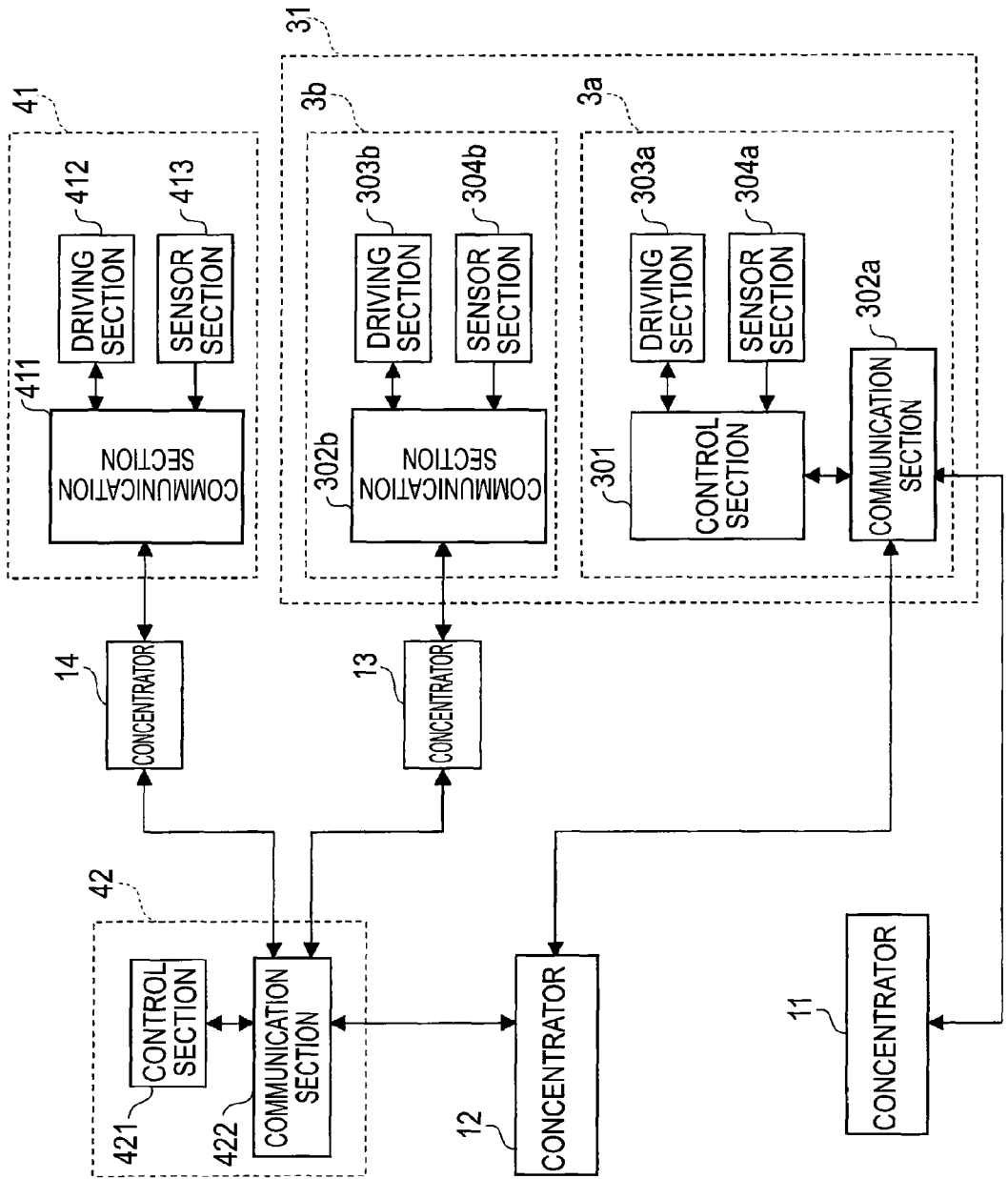
FIG. 7 is a diagram showing the outline of the configurations of the transport unit, a measuring unit and an information processing unit according to the embodiment.

FIG. 7 is a diagram showing the outline of the configurations of the transport unit 31, the measuring unit 41 and the information processing unit 42. In FIG. 7, for the sake of convenience, only one transport unit 31 and only one measuring unit 41 are shown. However, the transport units 32 and 33 and the other measuring units 41 also have the same configurations.

The transport unit 31 has a configuration in which a communication section 302b, a driving section 303b and a sensor section 304b are added to the insertion unit 22 of FIG. 6.

A communication section 302a performs data communication with the concentrators 11 and 12 and the communication section 302b performs data communication with the concentrator 13. A driving section 303a is controlled by a control section 301 and the driving section 303b is controlled by the information processing unit 42 via the communication section 302b. A sensor section 304a outputs a detection signal to the control section 301 and the sensor section 304b outputs a detection signal to the information processing unit 42 via the communication section 302b.

The communication section 302b, the driving section 303b and the sensor section 304b are included in the sample supply section 3b of FIG. 5 and the sections in the transport unit 31 other than the communication section 302b, the driving section 303b and the sensor section 304b are included in the sample relay section 3a of FIG. 5. The driving section 303a and the sensor section 304a include mechanisms for transporting and detecting sample racks L on the left table 330 and the rack transport sections 340 and 350 of FIG. 4, respectively. The driving section 303b and the sensor section 304b include mechanisms for transporting and detecting sample racks L on the right table 310 and the rack transport section 320 of FIG. 4, respectively.

The measuring unit 41 includes a communication section 411, a driving section 412 and a sensor section 413. The communication section 411 performs data communication with the concentrator 14. The driving section 412 and the sensor section 413 include mechanisms for transporting and detecting sample containers T in the measuring unit 41, respectively.

The information processing unit 42 has the same configuration as that of the transport controller 7 of FIG. 6. The control section 421 controls the sample supply section 3b of the transport unit 31 via a communication section 422 and the concentrator 13 and receives a detection signal of the sensor section 304b. In addition, the control section 421 controls the driving section 412 of the measuring unit 41 via the communication section 422 and the concentrator 14 and receives a detection signal of the sensor section 413.

Figure 8:
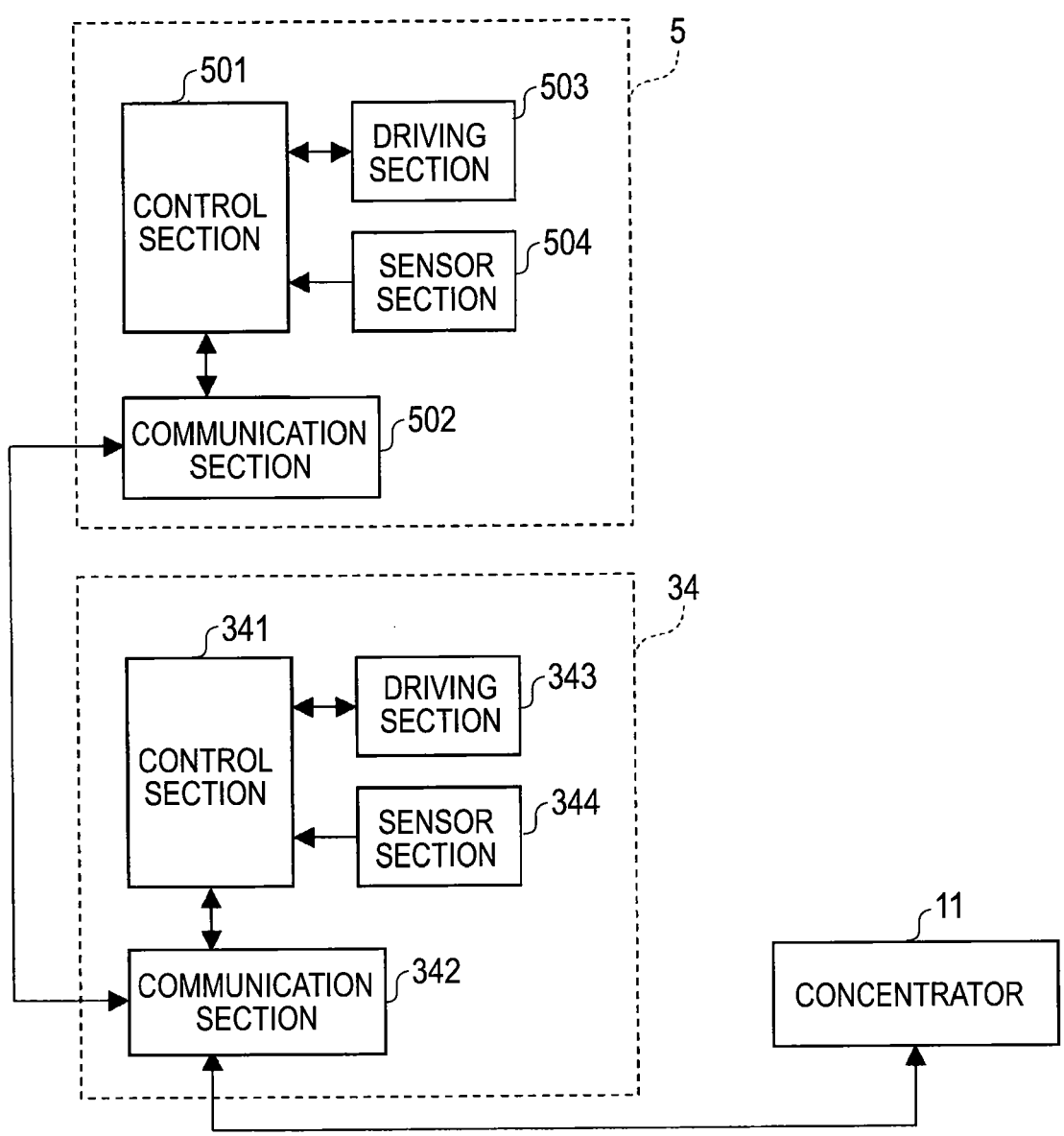
FIG. 8 is a diagram showing the outline of the configurations of the transport unit and a smear preparation apparatus according to the embodiment.

FIG. 8 is a diagram showing the outline of the configurations of the transport unit 34 and the smear preparation apparatus 5. The transport unit 34 and the smear preparation apparatus 5 have the same configuration as that of the insertion unit 22 of FIG. 6. The transport unit 34 includes a control section 341, a communication section 342, a driving section 343 and a sensor section 344, and the smear preparation apparatus 5 includes a control section 501, a communication section 502, a driving section 503 and a sensor section 504.

The communication section 342 of the transport unit 34 performs data communication with the concentrator 11. The communication section 342 is connected to the communication section 502 of the smear preparation apparatus 5 by a signal line and performs data communication with the communication section 502. When receiving a smear preparation instruction from the transport unit 34 via the communication section 502, the control section 501 of the smear preparation apparatus 5 suctions a sample from a sample container T on the measurement line of the transport unit 34 and prepares a smear.

Next, transport control of a sample rack L will be described with reference to FIGS. 9 to 18.

Figure 9B:
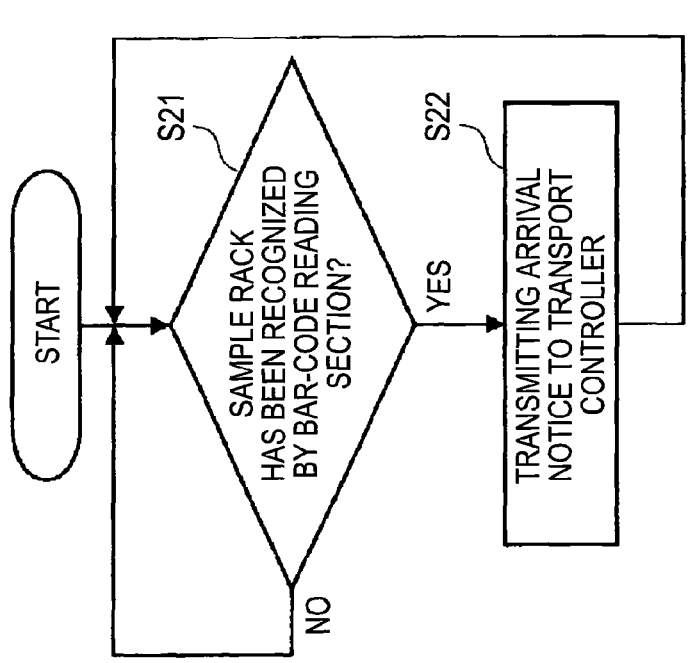
Figure 9A:
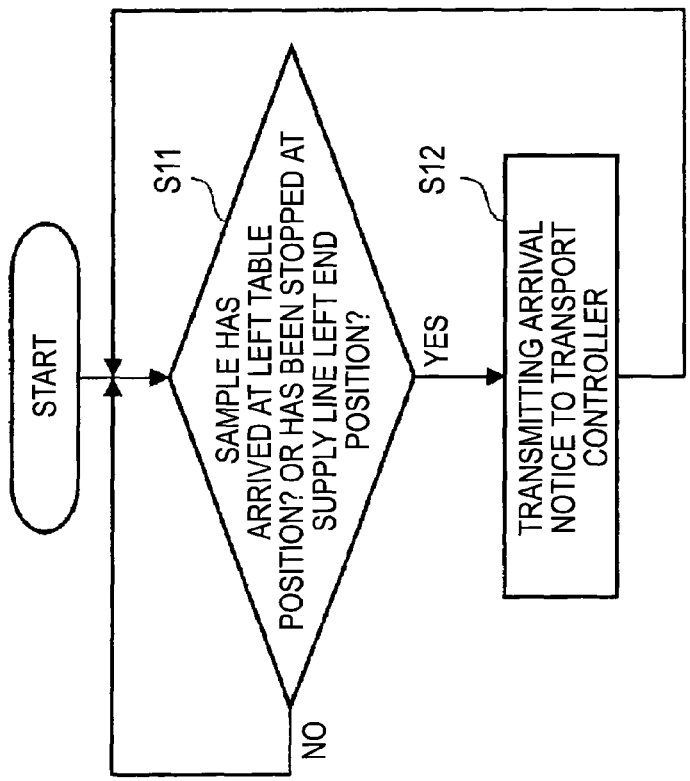

FIG. 9A is a flowchart showing an arrival notification process of the transport units 31 to 34 and FIG. 9B is a flowchart showing an arrival notification process of the output unit 23.

Referring to FIG. 9A, the control section 301 (control section 341) of the transport units 31 to 34 determines whether a sample rack L is positioned at the left table position or is stopped at the supply line left end position (S11). Such determination is performed on the basis of whether the sample rack L positioned at the left table position is detected by the sensors 334a and 334b or whether the sample rack L positioned at the supply line left end position is detected by the sensors 345a and 345b when the stopper 346 is dropped.

When determining that the sample rack L is positioned at the left table position or stopped at the supply line left end position (S11: YES), the control section 301 transmits an arrival notice to the transport controller 6 together with information about the position at which this sample rack L is positioned (S12). The arrival notification process is repeatedly performed in parallel in the transport units 31 to 34.

Referring to FIG. 9B, when the bar-code reading section 236 reads the rack ID of a sample rack L which is positioned at the rack ID reading position (S21: YES), the control section 237 of the output unit 23 transmits an arrival notice to the transport controller 6 (S22).

Here, when receiving the arrival notice from the transport units 31 to 34 and the output unit 23, the control section 601 of the transport controller 6 writes identification information of the sample rack L which is the source of the arrival notice in a table (hereinafter, referred to as a "priority table") set in the memory in the control section 601.

FIG. 9C is a flowchart showing an adding process of the priority table of the transport controller 6.

When receiving an arrival notice from any of the transport units 31 to 34 and the output unit 23 (S31: YES), the control section 601 of the transport controller 6 adds identification information of a sample rack L which is the source of the arrival notice in the last row of the priority table (S32).

Figure 10C:
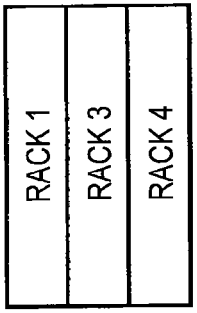
FIGS. 10A to 10E conceptually show priority tables according to the embodiment.
Figure 10E:
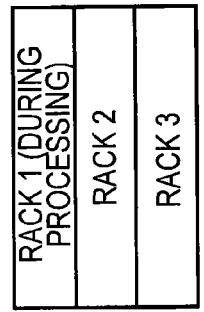
Figure 10B:
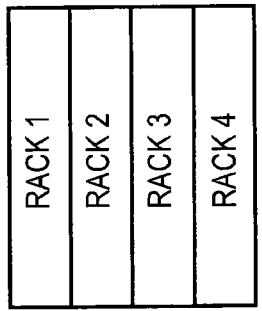
Figure 10D:
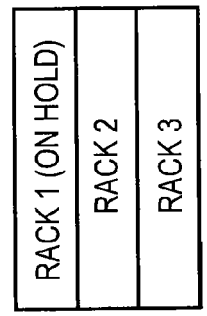
Figure 10A:
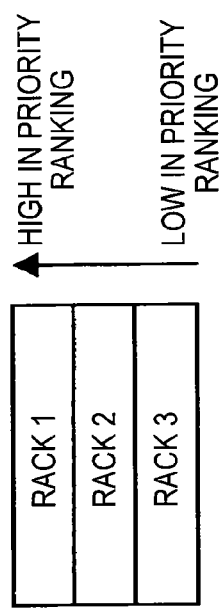

FIG. 10A is a diagram conceptually showing the priority table. In FIG. 10A, identification information (racks 1 to 3) of three sample racks L is written. Accordingly, it is found that the transport controller 6 has received the arrival notice in order of the racks 1 to 3. From this state, when the control section 601 of the transport controller 6 receives an arrival notice, identification information (for example, rack 4) of a sample rack L which is the source of the newly arrived arrival notice is added under the rack 3 as shown in FIG. 10B.

FIG. 9D is a flowchart showing a removal process of the priority table of the transport controller 6.

When receiving a rack discharge completion notice to be described later from any of the transport units 31 to 34 and the output unit 23 (S41: YES), the control section 601 of the transport controller 6 deletes from the priority table (S42) identification information of a sample rack L which is the source of this rack discharge completion notice. For example, when deleting identification information of the rack 2 from the priority table of FIG. 10B, the rack 1 does not change and the identification information of the racks 3 and 4 is pulled up by one row, so a state shown in FIG. 10C is made. The rack discharge completion notice will be described later with reference to FIGS. 14 and 15.

FIGS. 11A and 11B illustrate a flowchart showing a transport unit control process of the transport controller 6 based on the priority table. Such transport unit control process is executed at predetermined time intervals (for example, every one second) by the control section 601 of the transport controller 6. As described above, the transport destination of a sample rack L is determined to be the measuring unit 41 or the smear preparation apparatus 5 when the rack ID is read by the bar-code reading section 236 of the output unit 23. Hereinafter, the transport unit corresponding to the measuring unit 41 or the smear preparation apparatus 5 which is the transport destination is called a "destination".

The control section 601 sets a reference sample rack L to a sample rack L positioned at the top of the priority table (S101). Next, when the destination of this sample rack L is positioned behind (downstream side) the transport unit in which this sample rack L is positioned (S102: YES), the process proceeds to S107. On the other hand, when the destination of this sample rack L is not behind (downstream side), that is, when this sample rack L is transported toward the recovery unit 21 from the recovery line (S102: NO), the process proceeds to S103.

In S103, the control section 601 determines whether the supply line of this transport unit is on standby. Here, the standby state of the supply line of the transport unit is a state in which the belts 341a and 341b of the rack transport section 340 are stopped, the stopper 346 is lifted and a "recovery process" shown in FIG. 15A is not performed. That is, the state in which the supply line is on standby is a state in which the supply line is not used in the transportation of another sample rack. Even when the stopper 346 is dropped, it may be determined that the supply line is on standby. In addition, when the supply line is not used to transport another sample rack L at the point of time when the reference sample rack L is introduced to the supply line, it may be determined that the supply line is on standby. For example, even when the belts 341a and 341b operate for another sample rack at this point, it may be determined that the supply line is on standby when the belts 341a and 341b do not operate for another sample rack L at the point of time when the reference sample rack L is introduced to the supply line.

When the supply line of this transport unit is on standby (S103: YES), the control section 601 determines whether the recovery line of this transport unit is on standby. That is, the control section 601 determines whether the belt 351 of the rack transport section 350 is stopped and another sample rack L is placed on this belt 351 in the transport unit in which the sample rack L is placed.

When the recovery line of this transport unit is on standby (S104: YES), the control section 601 transmits a recovery instruction so as to perform the "recovery process" on this transport unit (S105). Accordingly, the reference sample rack L is positioned at the recovery line left end position. The "recovery process" will be described later with reference to FIG. 15A.

On the other hand, when the supply line of this transport unit is not on standby (S103: NO) and when the recovery line of this transport unit is not on standby (S104: NO), the process proceeds to S106.

Next, the control section 601 changes the reference destination in the priority table to the next-ranked sample rack L (S106) and returns the process to S102. Regarding the sample rack L which is the reference destination, when determination is made to be NO in S103 or S104, the sample rack L which is the reference destination in the priority table is set to "on hold" as shown in FIG. 10D. In addition, in S105, when a recovery instruction is made for the sample rack L which is the reference destination, the sample rack L which is the reference destination in the priority table is set to "during processing" as shown in FIG. 10E.

Next, in S107, the control section 601 determines whether the supply line of the transport unit which is ahead of (on the left of) this transport unit by one unit is on standby. In the following, "transport unit which is ahead by n units" indicates a transport unit which is disposed at the n-th unit position in the left direction from the transport unit in which a sample rack L which is a reference destination is positioned or the transport unit on the left of the output unit.

When the supply line of the transport unit which is ahead by one unit is on standby (S107: YES), the process proceeds to S108, and when the supply line of the transport unit which is ahead by one unit is not on standby (S107: NO), the process proceeds to S116.

In S108, the control section 601 determines whether the transport unit which is ahead of this transport unit by one unit is a destination of the reference sample rack L. When the transport unit which is ahead by one unit is not the destination (S108: NO), the process proceeds to S110. When the transport unit which is ahead by one unit is the destination (S108: YES), the control section 601 transmits a right introduction instruction so as to perform a "right introduction process" on the transport unit which is ahead by one unit and is on standby (S109). The "right introduction process" will be described later with reference to FIG. 14C.

In S110, the control section 601 determines whether the supply line of the transport unit which is ahead of this transport unit by two units is on standby. When the supply line of the transport unit which is ahead by two units is on standby (S110: YES), the process proceeds to S112. When the supply line of the transport unit which is ahead by two units is not on standby (S110: NO), the control section 601 transmits a holding instruction so as to perform a "holding process" on the transport unit which is ahead by one unit (S111). The "holding process" will be described later with reference to FIG. 14B.

In S112, the control section 601 determines whether the transport unit which is ahead of this transport unit by two units is a destination of the reference sample rack L. When the transport unit which is ahead by two units is the destination (S112: YES), the control section 601 transmits a right introduction instruction so as to perform the "right introduction process" on the transport unit which is ahead by two units and is on standby, and transmits a passing instruction so as to perform a "passing process" on the transport unit which is ahead by one unit and is on standby (S113). On the other hand, when the transport unit which is ahead by two units is not the destination, that is, when the destination is the unit which is ahead by three or more units (S112: NO), the control section 601 transmits a holding instruction so as to perform the "holding process" on the transport unit which is ahead by two units and transmits a passing instruction so as to perform the "passing process" on the transport unit which is ahead by one unit (S114). The "passing process" will be described later with reference to FIG. 14A.

In this manner, the corresponding transport units are instructed, and then in S115, the control section 601 transmits a discharge instruction so as to perform a "discharge process" on the output unit 23 or the transport unit in which the sample rack L which is the reference destination is positioned (S115). The "discharge process" will be described later with reference to FIGS. 15B and 15C.

Next, in S116, the control section 601 changes the reference destination in the priority table to a next-ranked sample rack L (S116) and returns the process to S102. Regarding the sample rack L which is the reference destination, when determination is made to be NO in S107, the sample rack L which is the reference destination in the priority table is set to "on hold" as shown in FIG. 10D. In addition, in S115, when a discharge instruction is made for the sample rack L which is the reference destination, the sample rack L which is the reference destination in the priority table is set to "during processing" as shown in FIG. 10E.

In S106 and S116, when there is no sample rack L which is ranked next to the sample rack L during the reference in the priority table, this transport unit control process is completed.

In the control process of FIGS. 11A and 11B, when the transport unit which is ahead by two or more units from the output unit or the transport unit in which the sample rack L which is the reference destination is positioned is the destination (S108: NO), the transport control is performed with the transport units as targets which are ahead by up to two units (S110 to S114). At this time, even when other sample racks L are positioned in the transport units which are ahead by up to two units, the sample rack L which is the reference destination is positioned at the position which is added to the priority table in advance of these other sample racks L. That is, in the control process of FIGS. 11A and 11B, with two transport units as control targets, among the sample racks L to be transported by these transport units, the sample rack L which is positioned at the position which is most rapidly added to the priority table is transported to these two transport units on a priority basis. However, in response to whether these two transport units are on standby, the transportation of the sample rack L is further controlled (S107: NO or S110: NO).

FIG. 12 is a flowchart showing a passing notification process of the transport units 31 to 33.

The control section 301 of the transport units 31 to 33 determines whether a sample rack L has crossed the supply line center position (S51). Such determination is carried out on the basis of whether the sample rack L positioned at the supply line center position has been detected by the sensors 344a and 344b.

When determining that the sample rack L has crossed the supply line center position (S51: YES), the control section 301 transmits a passing notice to the transport controller 6 (S52). The passing notification process is repeatedly performed in parallel in the transport units 31 to 33.

FIGS. 13A and 13B illustrate a flowchart showing a transport unit control process of the transport controller 6 when a passing notice is received. Such transport unit control process is executed when the control section 601 of the transport controller 6 receives a passing notice from any of the transport units 31 to 33. In addition, such transport unit control process is performed without referring to the priority table.

The control section 601 determines whether this transport unit is being subjected to the passing process (to be described later by using FIG. 14A) (S201). That is, the control section 601 determines whether the belts 341a and 341b of the rack transport section 340 of this transport unit are being driven and the stopper 346 is dropped. When this transport unit is being subjected to the passing process (S201: YES), the process proceeds to S202. When this transport unit is being not subjected to the passing process, that is, when this transport unit is being subjected to the holding process (to be described later by using FIG. 14B) (S201: NO), the process proceeds to S207.

In S202, the control section 601 determines whether the transport unit which is ahead of this transport unit by one unit is a destination of the sample rack L which is the source of the passing notice. When the transport unit which is ahead by one unit is the destination (S202: YES), the transport unit which is ahead by one unit is being subjected to the right introduction process and thus the process is completed. On the other hand, when the transport unit which is ahead by one unit is not the destination (S202: NO), the transport unit which is ahead by one unit is being subjected to the holding process and thus the process proceeds to S203.

In S203, the control section 601 determines whether the supply line of the transport unit which is ahead by two units is on standby. When the supply line of the transport unit which is ahead by two units is not on standby (S203: NO), the process is completed. In this case, the sample rack L is stopped at the supply line left end position in the transport unit which is ahead by one unit. On the other hand, when the supply line of the transport unit which is ahead by two units is on standby (S203: YES), the process proceeds to S204.

In S204, the control section 601 determines whether the transport unit which is ahead by two units is the destination of the sample rack L which is the source of the passing notice. When the transport unit which is ahead by two units is the destination (S204: YES), the control section 601 transmits a right introduction instruction so as to perform the "right introduction process" on the transport unit which is ahead by two units and transmits a passing instruction so as to perform the "passing process" on the transport unit which is ahead by one unit (S205). On the other hand, when the transport unit which is ahead by two units is not the destination (S204: NO), the control section 601 transmits a holding instruction so as to perform the "holding process" on the transport unit which is ahead by two units, and transmits a passing instruction so as to perform the "passing process" on the transport unit which is ahead by one unit (S206).

In S201, when it is determined that the transport unit which is the transmission source of the passing notice is being not subjected to the passing process, that is, when it is determined that this transport unit is being subjected to the holding process, in S207, the control section 601 determines whether the supply line of the transport unit which is ahead by one unit is on standby. When the supply line of the transport unit which is ahead by one unit is on standby (S207: YES), the process proceeds to S208, and when the supply line of the transport unit which is ahead by one unit is not on standby (S207: NO), the process is completed. When the determination is made to be NO in S207, the sample rack L is stopped at the supply line left end position in this transport unit.

Here, since the processes in S208 to S214 are the same as the processes in S108 to S114 of FIG. 11B, the description thereof will be omitted.

Next, when the processes in S209, S211, S213 and S214 are completed, the control section 601 transmits a passing instruction so as to perform the "passing process" on this transport unit (S215).

Figure 14B:
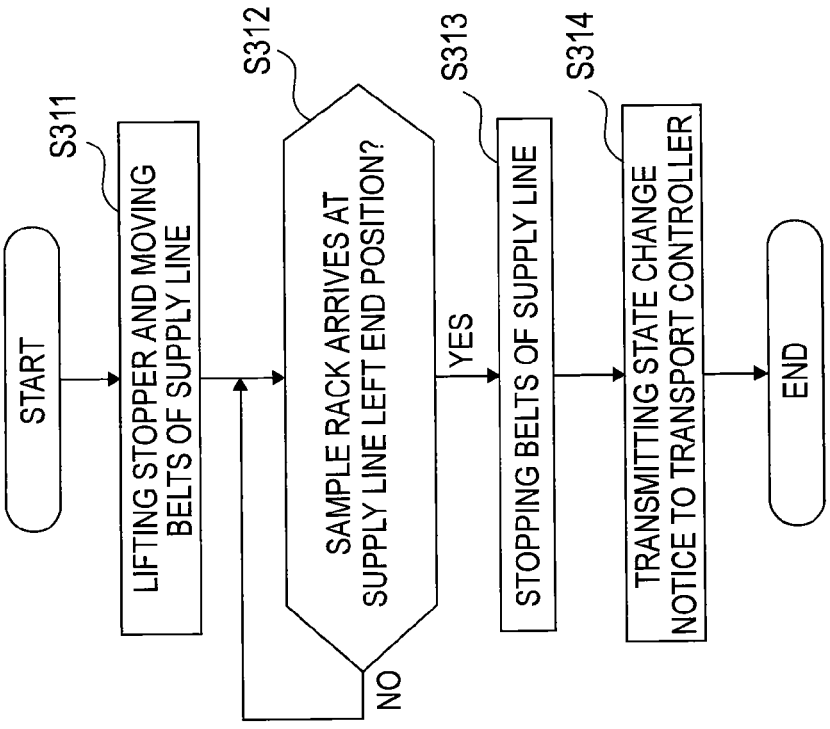
Figure 14A:
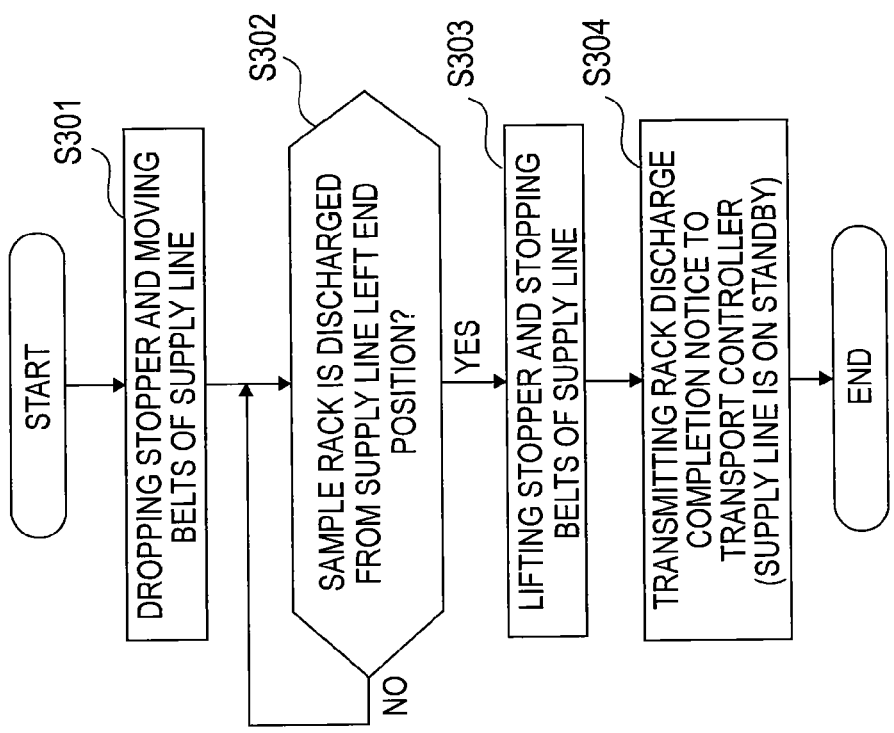

FIG. 14A is a flowchart showing the "passing process" of the transport units 31 to 33. When receiving a passing instruction from the transport controller 6, the control section 301 of the transport units 31 to 33 transmits an instruction reception completion notice to the transport controller 6 and performs the following process.

The control section 301 drops the stopper 346 and moves the belts 341a and 341b of the supply line (S301). The control section 301 determines whether a sample rack L is transported to the left from the right along the supply line and this sample rack L is discharged to the left transport unit from the supply line left end position. The control section 301 repeats the step S302 until the condition is satisfied. When the sample rack L positioned at the supply line left end position is not detected by the sensors 345a and 345b, it is determined that this sample rack L has been discharged to the left transport unit.

When the sample rack L is discharged from the supply line left end position (S302: YES), the control section 301 lifts the stopper 346 and stops the belts 341a and 341b of the supply line (S303). Next, the control section 301 transmits a rack discharge completion notice to the transport controller 6 (S304). Accordingly, the supply line of this transport unit is put in a standby state and thus the "passing process" is completed.

FIG. 14B is a flowchart showing the "holding process" of the transport units 31 to 33. When receiving a holding instruction from the transport controller 6, the control section 301 of the transport units 31 to 33 transmits an instruction reception completion notice to the transport controller 6 and performs the following process.

The control section 301 lifts the stopper 346 and moves the belts 341a and 341b of the supply line to transport a sample rack L to the left from the right along the supply line (S311). The control section 301 determines whether this sample rack L arrives at the supply line left end position (S312). The control section 301 repeats the step S312 until the condition is satisfied. When the sample rack L arrives at the supply line left end position, the sample rack L is stopped at this position by the stopper 346 and this sample rack L is detected by the sensors 345a and 345b. Accordingly, when the sample rack L arrives at the supply line left end position (S312: YES), the control section 301 stops the belts 341a and 341b of the supply line (S313). Next, the control section 301 transmits a state change notice showing that the sample rack L has arrives at the supply line left end position to the transport controller 6 (S314). Therefore, identification information of the sample rack L which has been positioned at the supply line left end position is added to the priority table. In this manner, the "holding process" is completed.

FIG. 14C is a flowchart showing the "right introduction process" of the transport units 31 to 34. When receiving a right introduction instruction from the transport controller 6, the control section 301 (control section 341) of the transport units 31 to 34 transmits an instruction reception completion notice to the transport controller 6 and performs the following process.

The control section 301 (control section 341) lifts the stopper 346, moves the belts 341a and 341b of the supply line and moves the rack pushing mechanism 342 up to a position at which the wall section 342a is hung onto the supply line to transport a sample rack L to the left from the right along the supply line (S321). The control section 301 (control section 341) determines whether this sample rack L arrives at the supply line right end position (S322). The control section 301 (control section 341) repeats the step S322 until the condition is satisfied. When the sample rack L arrives at the supply line right end position, the sample rack L is stopped at this position by the wall section 342a of the rack pushing mechanism 342 and this sample rack L is detected by the sensors 343a and 343b.

When the sample rack L arrives at the supply line right end position (S322: YES), the control section 301 (control section 341) further moves the rack pushing mechanism 342 backward to push the sample rack L at the supply line right end position to the right table 310 (S323). Then, the control section 301 (control section 341) returns the rack pushing mechanism 342 to a space between the rack transport sections 340 and 350 and stops the belts 341a and 341b of the supply line (S324). Next, the control section 301 (control section 341) transmits a state change notice to the transport controller 6 (S325). Accordingly, the "right introduction process" is completed.

FIG. 15A is a flowchart showing the "recovery process" of the transport units 31 to 34. When receiving a recovery instruction from the transport controller 6, the control section 301 (control section 341) of the transport units 31 to 34 transmits an instruction reception completion notice to the transport controller 6 and performs the following process.

First, the control section 301 (control section 341) puts the supply line in a non-standby state (S331). Next, the control section 301 (control section 341) drops the partition section 352 and pushes a sample rack L which is positioned at the left table position forward by the rack input mechanism 333 to (S332). The control section 301 (control section 341) determines whether this sample rack L arrives at the recovery line left end position (S333). The control section 301 (control section 341) repeats the step S333 until the condition is satisfied. When the sample rack L arrives at the recovery line left end position, this sample rack is detected by the sensors 353a and 353b.

When the sample rack L arrives at the recovery line left end position (S333: YES), the control section 301 (control section 341) returns the rack input mechanism 333 up to the left table 320 and lifts the partition section 352 (S334). Next, the control section 301 (control section 341) transmits a rack discharge completion notice to the transport controller 6 (S335). Accordingly, the supply line of this transport unit is put in a standby state and thus the "recovery process" is completed. When receiving the rack discharge completion notice which is transmitted in S335, the transport controller 6 deletes this sample rack L from the priority table as shown in, for example, FIG. 9D.

FIG. 15B is a flowchart showing the "discharge process" of the transport units 31 to 33. When receiving a discharge instruction from the transport controller 6, the control section 301 of the transport units 31 to 33 transmits an instruction reception completion notice to the transport controller 6 and performs the following process. This "discharge process" is performed when a sample rack L which is positioned at the left table position or at the supply line left end position is discharged to the transport unit on the left side of this transport unit.

The control section 301 drops the stopper 346 and moves the belts 341a and 341b of the supply line (S341). Here, when a sample rack L which is positioned at the left table position is discharged, this sample rack L is positioned at the supply line left end position by the rack input mechanism 333 and then the stopper 346 and the belts 341a and 341b are driven.

The control section 301 determines whether the sample rack L is discharged to the left transport unit from the supply line left end position (S342). The control section 301 repeats the step S342 until the condition is satisfied.

When the sample rack L is discharged from the supply line left end position (S342: YES), the control section 301 stops the belts 341a and 341b of the supply line (S343). Next, the control section 301 transmits a rack discharge completion notice to the transport controller 6 (S344). Accordingly, the "discharge process" is completed. When receiving the rack discharge completion notice which is transmitted in S344, the transport controller 6 deletes this sample rack L from the priority table as shown in FIG. 9D.

FIG. 15C is a flowchart showing the "discharge process" of the output unit 23. When receiving a discharge instruction from the transport controller 6, the control section 237 of the output unit 23 transmits an instruction reception completion notice to the transport controller 6 and performs the following process.

The control section 237 pushes a sample rack L which is positioned at the rack ID reading position to the supply line of the transport unit 31 by moving the rack output mechanism 235 in the left direction (S351). The control section 237 determines whether a next sample rack L of this sample rack L is made to be capable of being discharged (S352). The control section 237 repeats the step S352 until the condition is satisfied. That is, the step S352 is repeated until this sample rack L is transported to the transport unit 31 from the output unit 23 and the rack output mechanism 235 returns to the right end position immediately in front of the output unit 23.

When the next sample rack L is made to be capable of being discharged (S352: YES), the control section 237 transmits a rack discharge completion notice to the transport controller 6 (S353). Accordingly, the "discharge process" of the output unit 23 is completed. When receiving the rack discharge completion notice which is transmitted in S353, this sample rack L is deleted from the priority table as shown in, for example, FIG. 9D.

FIGS. 16 and 17 are diagrams illustrating that a sample rack L is transported up to a destination by controlling the transport unit. In FIGS. 16 and 17, schematic diagrams showing the output unit 23 and the transport units 31 to 33 are shown. For the sake of convenience, the transport unit 34 will be omitted in the drawings.

Referring to FIG. 16A, as shown in the drawing, sample racks L (hereinafter, referred to as a "rack 1", a "rack 2" and a "rack 3") are included in the output unit 23 and the transport units 32 and 33, respectively. The destination of the rack 1 is the transport unit 33, the rack 2 has no destination (recovery only) and the destination of the rack 3 is the transport unit 34.

When the racks 1 to 3 arrive in order at the rack ID reading position in the output unit 23, at the left table position in the transport unit 32 and at the left table position in the transport unit 33, identification information of the racks 1 to 3 are added to the last row of the priority table in order. Accordingly, priority rankings of the racks 1 to 3 in the priority table are in order of the racks 1 to 3 as shown in FIG. 16E.

When the rack 1 is a transport target, the rack ID reading position in the output unit 23 corresponds to a "first position" in the claims and the left table positions in the transport units 31 and 32 correspond to a "Second position" in the claims.

In FIG. 16A, a rack which is shown by the broken line in FIG. 16A and positioned at the supply line left table position or the left table position in the transport unit 31 is a transport target, these left table position or the supply line left end position correspond to the "first position" in the claims, and the left table positions in the transport units 32 and 33 correspond to the "Second position" in the claims.

Hereinafter, a control operation when the rack 1 is positioned at the rack ID reading position (first position) in the output unit 23 as in FIG. 16A will be described. However, also in the case in which the rack which is positioned at the broken line position (first position) of FIG. 16A is a control target, the following control operation is performed with the transport units 32 and 33 as control targets.

The control section 601 of the transport controller 6 sets a reference sample rack L in the priority table to the rack 1 in accordance with the control order of FIGS. 11A and 11B and controls the transport unit so as to transport the rack 1. That is, since the destination of the rack 1 is the transport unit 33 which is ahead by three units and the supply lines of the transport units 31 and 32 are on standby, a holding instruction is transmitted to the transport unit 32 and a passing instruction is transmitted to the transport unit 31. In addition, a discharge instruction is transmitted to the output unit 23 and the rack 1 starts to be transported. Accordingly, the reference destination in the priority table is changed to one which is below by one row. At this time, the priority table is as shown in FIG. 16F.

Referring to FIG. 16B, next, the rack 2 starts to be processed. However, since the supply line of the transport unit 32 is not on standby, the reference destination in the priority table is changed to one which is below by one row without the transportation of the rack 2 and the rack 3 starts to be processed. At this time, the priority table is as shown in FIG. 16G. In addition, although the transport unit control process of FIGS. 11A and 11B is also performed at predetermined time intervals during this period, it is determined that the rack 1 is being subjected to the process and the rack 2 is on hold and thus the processing of the racks 1 and 2 is not performed. When the rack 3 starts to be processed, the rack 3 is discharged to the transport unit 34 which is the destination thereof.

When the rack 1 is discharged from the output unit 23 and the transport controller 6 receives a rack discharge completion notice, the rack 1 is deleted from the priority table. In the same manner, when the rack 3 is discharged from the transport unit 33 and the transport controller 6 receives a rack discharge completion notice, the rack 3 is deleted from the priority table. Accordingly, the priority table is as shown in FIG. 16H.

As shown in FIG. 16C, when the rack 1 passes through the supply line center position in the transport unit 31, the transport unit is controlled in accordance with the control order of FIGS. 13A and 13B. That is, since the transport unit 31 is being subjected to the passing process, the supply line of the transport unit 33 is on standby, and the destination of the rack 1 is the unit which is ahead by two units, a right introduction instruction is transmitted to the transport unit 33 and a passing instruction is transmitted to the transport unit 32. Accordingly, as shown in FIG. 16D, in the transport unit 33, the right introduction process is performed and the passing process is performed in the transport unit 32.

In the case in which when the rack 1 passes through the supply line center position in the transport unit 31 as shown in FIG. 16C, the transport unit 33 is not on standby, and then when the rack 1 passes through the supply line center position in the transport unit 32, the rack 3 is being transported and the transport unit 33 is thus not on standby, the rack 1 is stopped at the supply line left end position of the transport unit 32 as shown in FIG. 17A. Accordingly, the rack 1 is added to the last row of the priority table. In this case, the rack 1 cannot move until the recovery process of the rack 3 is completed.

Next, when the rack 1 proceeds in the left direction from the state of FIG. 16D and passes through the supply line center position of the transport unit 32 as shown in FIG. 17B, determination is made to be YES in S201 of FIG. 13A and the passing process of the transport unit 32 and the right introduction process of the transport unit 33 are continued. At this time, the priority table is as shown in FIG. 17F.

Referring to FIG. 17C, when the rack 1 is transported to the transport unit 33 from the transport unit 32 and then the transport unit control process of FIGS. 11A and 11B which is performed at predetermined time intervals is executed, the rack 2 is positioned at the top of the priority table and thus the rack 2 starts to be processes. At this time, since the supply line and the recovery line of the transport unit 32 are on standby, a recovery instruction is transmitted to the transport unit 32 and the rack 2 is transported up to the recovery line left end position as shown in FIG. 17D. Accordingly, as shown in FIG. 17H, the rack 2 is deleted from the priority table.

FIG. 18 is a diagram showing contents of the communication which is performed between the transport units 31 to 33, the output unit 23 and the transport controller 6 in the transport control of the transport units 31 to 33 shown in FIGS. 16 and 17. In FIG. 18, for the sake of convenience, only the transport control related to the rack 1 is shown.

When the bar-code reading section 236 of the output unit 23 reads the rack ID, an arrival notice is transmitted to the transport controller 6 from the output unit 23 as shown in S22 of FIG. 9B. At this time, since the transport units 31 and 32 are on standby, the transport controller 6 transmits a holding instruction to the transport unit 32 which is ahead by two units and transmits a passing instruction to the transport unit 31 which is ahead by one unit as shown in S114 of FIGS. 11A and 11B.

In greater detail, first, the transport controller 6 transmits a holding instruction to the transport unit 32 (S402). When receiving the holding instruction, the transport unit 32 transmits an instruction reception completion notice to the transport controller 6 (S403). Next, the transport controller 6 transmits a passing instruction to the transport unit 31 (S404). When receiving the passing instruction, the transport unit 31 transmits an instruction reception completion notice to the transport controller 6 (S405). In this manner, when the transport units on the downstream side are instructed first, the sample rack L can be prevented from being transported mistakenly to the transport units on the downstream side in the case in which an error occurs in the transport units on the downstream side.

Next, the transport controller 6 transmits a discharge instruction to the output unit 23 as shown in S115 of FIG. 11B (S406). When receiving the discharge instruction, the output unit 23 transmits an instruction reception completion notice to the transport controller 6 (S407). After that, the output unit 23 transmits a rack discharge completion notice to the transport controller 6 as shown in S353 of FIG. 15C (S408). Accordingly, this sample rack L is deleted from the priority table.

Then, when the sample rack L which is output to the transport unit 31 passes through the supply line center position in the transport unit 31, a passing notice is transmitted to the transport controller 6 as shown in S52 of FIG. 12 (S409). Accordingly, the transport unit control process of FIGS. 13A and 13B is executed, and as shown in S205 of FIG. 13A, a right introduction instruction is transmitted to the transport unit 33 which is ahead by two units (S410) and a passing instruction is transmitted to the transport unit 32 which is ahead by one unit (S412). When receiving the right introduction instruction and the passing instruction, respectively, the transport units 33 and 32 transmit an instruction reception completion notice to the transport controller 6 (S411, S413).

Then, when this sample rack L is discharged from the transport unit 31, a rack discharge completion notice is transmitted to the transport controller 6 as shown in S304 of FIG. 14A (S414). Next, when this sample rack L passes through the supply line center position in the transport unit 32, a passing notice is transmitted to the transport controller 6 (S415). At this time, although the transport unit control process of FIGS. 13A and 13B is executed, determination is made to be YES in S202 of FIG. 13A and thus the transport unit control is not newly performed.

Then, when this sample rack L is discharged from the transport unit 32, a rack discharge completion notice is transmitted to the transport controller 6 as in S414 (S416). After that, in the "right introduction process" which is executed in the transport unit 33, this sample rack L is pushed to the right table 310 from the supply line right end position, and then as shown in FIG. 14C, a state change notice is transmitted to the transport controller 6 from the transport unit 33 (S417). Accordingly, the transport controller 6 can know that this sample rack has been moved to the right table of the transport unit 33.

According to the embodiments of the present invention, as shown in FIGS. 11A and 11B, sample racks are transported by the transport units 31 to 34 and the output unit 23 in order from the sample rack L which is positioned at the top of the priority table. That is, in transporting a reference sample rack L, when the supply lines of the transport unit which is ahead by one unit and the transport unit which is ahead by two units are on standby, instructions are transmitted for transporting this sample rack L to these transport units. Accordingly, it is not necessary to put this sample rack L on hold in the transport unit which is ahead by one unit before the sample rack L is discharged to the transport unit which is ahead by two units, and thus this sample rack L can be transported smoothly to the destination. In addition, since the transport units other than the transport unit which is ahead by one unit and the transport unit which is ahead by two units can be used to transport other sample racks which are low in priority ranking, the transport operation of other sample racks which are low in priority ranking can also be smoothly performed.

In addition, according to the embodiments of the present invention, when a sample rack L passes through the supply line center position, as shown in FIGS. 13A and 13B, when the supply lines of the transport unit which is ahead by one unit and the transport unit which is ahead by two units are on standby, instructions are transmitted for transporting this sample rack L to these transport units, respectively. Accordingly, since this sample rack L is not stopped in the transport unit which is ahead by one unit, this sample rack L can be transported smoothly to the transport unit which is ahead by two units from the transport unit which is ahead by one unit.

In addition, in the processes of FIGS. 11 and 13, even when the supply line of the transport unit which is ahead by one unit is on standby but the supply line of the transport unit which is ahead by two units is not on standby, this sample rack L is transported up to the transport unit which is ahead by one unit. Accordingly, since the sample rack L is transported to the downstream side as much as possible, transport efficiency can be increased.

As described above, the embodiments of the present invention have been described. However, the embodiments of the present invention are not limited thereto.

For example, in the above-described embodiments, blood is exemplified as a measurement target. However, urine can also be a measurement target. That is, the present invention can also be applied to a sample processing system examining urine and a clinical sample processing system examining other clinical samples.

In addition, in the above-described embodiments, the sample processing system 1 includes the four transport units 31 to 34. However, the present invention is not limited thereto. The sample processing system 1 may include three transport units and also may include five or more transport units.

In addition, in the above-described embodiments, as shown in FIGS. 11 and 13, the transport unit which is ahead by one unit and the transport unit which is ahead by two units are control targets. However, the present invention is not limited thereto. The control may be performed on the basis of the priority rankings of sample racks L with transport units as control targets which are ahead by up to n units (n is an integer equal to or greater than 1). In this case, when supply lines of the n transport units which are the control targets are on standby, a reference sample rack L on the priority table is transported by the supply lines of the n transport units, and when the transport unit on the downstream side is not on standby, the sample rack is transported by the transport unit on the upstream side which is on standby up to a position at which the sample rack can be transported.

In addition, in the above-described embodiments, the sample processing system has been described which introduces a sample rack to the measurement line from the supply line and discharges a sample rack in which the measurement has been completed to the supply line from the measurement line. However, the present invention is not limited thereto. A sample processing system may be provided in which a measuring unit suctions and measures a sample from a sample container stored in a sample rack positioned on a supply line, and after the suction of the sample, the sample rack is transported to the downstream side by the supply line.

In addition, in the above-described embodiments, the transport units 31 to 34 are connected to each other so as to directly deliver sample racks. However, the present invention is not limited thereto. A relay transport unit which receives a sample rack from the upstream transport unit and hands it to the transport unit on the downstream side may be provided between the transport units.

In addition, in the above-described embodiments, in Steep S113, a passing instruction is transmitted so as to perform the "passing process" on the transport unit which is ahead by one unit and a right introduction instruction is transmitted so as to perform the "right introduction instruction" on the transport unit which is ahead by two units. However, the present invention is not limited thereto. After a sample rack is introduced to the supply line of the transport unit which is ahead by one unit and before the sample rack arrives at the "supply line left end position", a passing instruction may be transmitted to the transport unit which is ahead by one unit and a right introduction instruction may be transmitted to the transport unit which is ahead by two units.

In addition, in the above-described embodiments, transport instructions are transmitted to the transport units which are ahead by up to two units. However, this is not limited to the transport units which are ahead by up to two units and a transport instruction may be transmitted to a transport unit which is ahead by three units.

Various modifications can be made in the embodiment of the present invention within the scope of the technical thoughts which are shown in the claims.

What is claimed is:

1. A sample processing system comprising:
a plurality of sample processing units;
an input/output unit configured to receive sample racks and to transport the sample racks along a transport path to each of the plurality of sample processing units, the input/output unit equipped with a reading section that reads a sample rack ID and a sample ID of containers in each sample rack;
a plurality of sample transport units coupled to the input/output unit by the sample transport path that transport the sample racks to the plurality of sample processing units, wherein each of the plurality of sample transport units is provided corresponding to each of the plurality of sample processing units; and
a control section, the control section determines which of the plurality of sample processing units is to process samples in each container based on information acquired by the reading section,
wherein the plurality of sample transport units includes at least a first sample transport unit, a second sample transport unit adjacent to the first sample transport unit and a third sample transport unit adjacent to the second sample transport unit in order from the upstream in a transport direction,
each of the sample transport units includes a transport path for transporting a sample rack to another sample transport unit on the downstream side and a transport member for moving a sample rack on the transport path, the transport member is configured to drive independently from transport members in other transport units, each of the transport paths has a beginning end and a terminal end,
wherein a terminal end of the transport path of the first sample transport unit and a beginning end of the transport path of the second sample transport unit are adjacent, and the transport path of the first sample transport unit transmits the sample rack to the transport path of the second sample transport unit,
a terminal end of the transport path of the second sample transport unit and a beginning end of the transport path of the third sample transport unit are adjacent, and the transport path of the second sample transport unit transmits the sample rack to the transport path of the third sample transport unit,
the first sample transport unit includes a sensor for detecting that a sample rack arrives at a predetermined position, and
the transport member is further configured for transporting a sample rack which is to be introduced to the first sample transport unit to a destination sample transport unit which is located downstream of the second sample transport unit, wherein each of the sample transport units further includes a pushing member, each of the pushing members configured to be located at a first position that does not interfere with the sample rack passing through each of the transport paths and at a second position that interferes with the sample rack to stop the sample rack on each of the transport paths, the control section performs the following process including:

determining a destination sample transport unit for a selected sample rack among the plurality of sample transport units;

when the third sample transport unit is determined to the destination sample transport unit, moving the transport members of the first and second sample transport units and positioning the pushing members of the first and second sample transport units at the first position to transport the selected sample rack to the third sample transport unit; and in response to detecting arrival of the selected sample rack at the sensor of the first sample transport unit, starting to move the transport member of the third sample transport unit; and positioning the pushing member of the third sample transport unit at the second position to stop the selected sample rack by the pushing member and then moving the pushing member toward the third sample processing unit from the second position.

2. The sample processing system of claim 1 wherein when the selected sample rack is transported out of the transport path of the first sample transport unit, the control section stops the transport member of the first sample transport unit.

3. The sample processing system of claim 1, wherein the control section controls the sample transport units to transport a plurality of sample racks according to a priority order.

4. The sample processing system of claim 3, wherein each of the sample transport units further comprises an introduction path for introducing a sample rack on the transport path to a sample processing unit which is provided to correspond to the sample transport unit and for returning it onto the transport path, the transport path has a first predetermined position, and the introduction path has a second predetermined position, and the control section gives a higher priority to a sample rack which arrives at first or second predetermined position earlier.

5. The sample processing system of claim 1, wherein the transport member comprises a belt extending along the transport path.

6. A sample processing system comprising:
a plurality of sample processing units;
an input/output unit configured to receive sample racks and to transport the sample racks along a transport path to each of the plurality of sample processing units, the input/output unit equipped with a reading section that reads a sample rack ID and a sample ID of containers in each sample rack;
m (m is an integer equal to or greater than 3) pieces of sample transport units for transporting a sample rack to each of the sample processing units, wherein each of the sample transport units is provided corresponding to each of the plurality of sample processing units,
wherein each of the sample transport units has a transport path coupled to the input/output unit by the sample transport path for transporting a sample rack to other sample transport units on the downstream side in a transport direction and a transport member for moving a sample rack on the transport path, the transport member configured to drive independently from transport members included in other transport units, each of the transport paths has a beginning end and a terminal end, and a first sample transport unit includes a sensor for detecting that a sample rack arrives at a predetermined position, wherein each of the sample transport units further includes a pushing member, each of the pushing members configured to be located at a first position that does not interfere with the sample rack passing through each of the transport paths and at a second position that interferes with the sample rack to stop the sample rack on each of the transport paths, a terminal end of the transport path of a sample transport unit and a beginning end of the transport path of the other sample transport unit arranged in a downstream side of the transport unit are adjacent, and the transport path of the sample transport unit transmits the sample rack to the transport path of the other sample transport unit, and a control section that determines which of the plurality of sample processing units is to process samples in each container based on information acquired by the reading section, wherein in order to transport a target sample rack to a third sample transport unit through the first and second sample transport units, the control section controls the first and second sample transport units by moving the transport members of the first and second sample transport units and positioning the pushing members of the first and second sample transport units at the first position to transport the target sample rack to the third transport unit, in response to detecting arrival of the target sample rack at the predetermined position in the transport path of the first sample transport unit by the sensor, starting to move the transport member of a third sample transport unit located next to the second sample transport unit, and positioning the pushing member of the third sample transport unit at the second position to stop the target sample rack by the pushing member and then moving the pushing member toward the third sample processing unit from the second position.

7. A transport control method for a plurality of sample transporting units coupled to an input/output unit configured to receive sample racks and to transport the sample racks along a transport path to each of the plurality of sample transport units, where the input/output unit equipped with a reading section that reads a sample rack 10 and a sample ID of containers in each sample rack, wherein each of the plurality of sample transporting units is provided corresponding to each of a plurality of sample processing units, each of the sample transporting units has a transporting member configured to drive independently from transport members included in other transport units, each of the transport members has a beginning end and a terminal end, a terminal end of the transport path of a sample transport unit and a beginning end of the transport path of the other sample transport unit arranged in a downstream side of the transport unit are adjacent, and the transport path of the sample transport unit transmits the sample rack to the transport path of the other sample transport unit, wherein each of the sample transport units further includes a pushing member, each of the pushing members configured to be located at a first position that does not interfere with the sample rack passing through each of the transport paths and at a second position that interferes with the sample rack to stop the sample rack on each of the transport paths, the method comprising computer executable steps executed by at least one processor of a computer system to implement:
- determining which of the plurality of sample transport units is to receive each sample rack based on information acquired by the reading section,
- controlling first and second sample transport units so as to move transport members of the first and second sample transport units and to position the pushing members of the first and second sample transport units at the first position to transport a sample rack which is to be introduced to the first sample transport unit toward a third sample transport unit,
- wherein the first transport unit includes a sensor for detecting that a sample rack arrives at the predetermined position; and
- controlling a third sample transport unit so as to move a transport member sample rack arrives at predetermined position on the first transport unit,
- the third transport unit is controlled to move the transport member upon reception of a detection signal from the sensor of the first sample transport unit,
- positioning the pushing member of the third sample transport unit at the second position to stop the sample rack on the third transport path by the pushing member and then moving the pushing member toward the third sample processing unit from the second position.

8. The transport control method of claim 7, wherein when the sample rack is transported out of the transport path of the first sample transport unit, the first sample transport unit is controlled to stop the transport member of the first sample transport unit.

9. The transport control method of claim 7, wherein the first, second and third transport units are controlled to transport a plurality of sample racks according to a priority order.

10. The transport control method of claim 7,
- wherein each of the first, second and third sample transport units further comprises an introduction path for introducing a sample rack on the transport path to a sample processing unit which is provided to correspond to the sample transport unit and for returning it onto the transport path,
- the transport path has a first predetermined position, and the introduction path has a second predetermined position, and a higher priority is given to a sample rack which arrives at first or second predetermined position earlier.

* * * * *